US011612574B2

(12) United States Patent
Galer

(10) Patent No.: US 11,612,574 B2
(45) Date of Patent: Mar. 28, 2023

(54) METHOD OF TREATING PATIENTS INFECTED WITH SEVERE ACUTE RESPIRATORY SYNDROME CORONAVIRUS 2 (SARS-COV-2)

(71) Applicant: ZOGENIX INTERNATIONAL LIMITED, Berkshire (GB)

(72) Inventor: Bradley S. Galer, West Chester, PA (US)

(73) Assignee: ZOGENIX INTERNATIONAL LIMITED, Berkshire (GB)

( * ) Notice: Subject to any disclaimer, the term of this patent is extended or adjusted under 35 U.S.C. 154(b) by 8 days.

(21) Appl. No.: 17/357,388

(22) Filed: Jun. 24, 2021

(65) Prior Publication Data

US 2022/0016053 A1 Jan. 20, 2022

Related U.S. Application Data

(60) Provisional application No. 63/058,334, filed on Jul. 29, 2020, provisional application No. 63/054,397, filed on Jul. 21, 2020, provisional application No. 63/053,162, filed on Jul. 17, 2020.

(51) Int. Cl.

| | |
|---|---|
| *A61K 31/137* | (2006.01) |
| *A61P 31/14* | (2006.01) |
| *A61K 31/522* | (2006.01) |
| *A61K 31/7072* | (2006.01) |
| *A61K 33/30* | (2006.01) |
| *A61K 45/06* | (2006.01) |

(52) U.S. Cl.

CPC .......... *A61K 31/137* (2013.01); *A61K 31/522* (2013.01); *A61K 31/7072* (2013.01); *A61K 33/30* (2013.01); *A61K 45/06* (2013.01); *A61P 31/14* (2018.01)

(58) Field of Classification Search

None

See application file for complete search history.

(56) References Cited

U.S. PATENT DOCUMENTS

| | | | |
|---|---|---|---|
| 3,117,160 | A | 1/1964 | Holland |
| 3,198,833 | A | 8/1965 | Beregi |
| 3,198,834 | A | 8/1965 | Beregi et al. |
| 3,759,979 | A | 9/1973 | Beregi et al. |
| 4,309,445 | A | 1/1982 | Wurtman |

(Continued)

FOREIGN PATENT DOCUMENTS

| | | |
|---|---|---|
| CN | 1425167 | 6/2003 |
| CN | 103025301 | 4/2013 |

(Continued)

OTHER PUBLICATIONS

Rawson et al. (Clinical Infectious Diseases, May 2, 2020;71(9):2459-68).*

(Continued)

*Primary Examiner* — Bong-Sook Baek

(74) *Attorney, Agent, or Firm* — Bret E. Field; Bozicevic, Field & Francis LLP

(57) ABSTRACT

Provided is a method of treating a patient infected with severe acute respiratory syndrome coronavirus 2 (SARS-CoV-2), comprising: determining the patient has been infected with SARS-CoV-2; and administering to the patient a therapeutically effective dose of fenfluramine.

20 Claims, 4 Drawing Sheets

(56) References Cited

U.S. PATENT DOCUMENTS

| | | | |
|---|---|---|---|
| 4,452,815 | A | 6/1984 | Wurtman |
| 4,824,987 | A | 4/1989 | Kleeman |
| 4,857,553 | A | 8/1989 | Ward et al. |
| 5,587,398 | A | 12/1996 | Elmaleh et al. |
| 5,808,156 | A | 9/1998 | Cannata et al. |
| 5,811,586 | A | 9/1998 | Cannata et al. |
| 5,834,477 | A | 11/1998 | Mioduszewski |
| 5,985,880 | A | 11/1999 | Chang |
| 6,045,501 | A | 4/2000 | Elsayed et al. |
| 6,315,720 | B1 | 11/2001 | Williams et al. |
| 6,561,976 | B2 | 5/2003 | Elsayed et al. |
| 6,561,977 | B2 | 5/2003 | Williams et al. |
| 6,599,901 | B1 | 7/2003 | Flohr |
| 6,755,784 | B2 | 6/2004 | Williams et al. |
| 6,869,399 | B2 | 3/2005 | Williams et al. |
| 6,908,432 | B2 | 6/2005 | Elsayed et al. |
| 7,141,018 | B2 | 11/2006 | Williams et al. |
| 7,585,493 | B2 | 9/2009 | Hale |
| 7,668,730 | B2 | 2/2010 | Reardan et al. |
| 7,765,106 | B2 | 7/2010 | Reardan et al. |
| 7,765,107 | B2 | 7/2010 | Reardan et al. |
| 7,797,171 | B2 | 9/2010 | Reardan et al. |
| 7,874,984 | B2 | 1/2011 | Elsayed et al. |
| 7,895,059 | B2 | 2/2011 | Reardan et al. |
| 7,959,566 | B2 | 6/2011 | Williams et al. |
| 8,204,763 | B2 | 6/2012 | Elsayed et al. |
| 8,263,650 | B2 | 9/2012 | Cook et al. |
| 8,315,886 | B2 | 11/2012 | Williams et al. |
| 8,386,274 | B1 | 2/2013 | Pinsonneault |
| 8,457,988 | B1 | 6/2013 | Reardan et al. |
| 8,589,182 | B1 | 11/2013 | Reardan et al. |
| 8,589,188 | B2 | 11/2013 | Elsayed et al. |
| 8,626,531 | B2 | 1/2014 | Williams et al. |
| 8,731,963 | B1 | 5/2014 | Reardan et al. |
| 9,125,900 | B2 | 9/2015 | Meyer |
| 9,549,909 | B2 | 1/2017 | Ceulemens |
| 9,603,814 | B2 | 3/2017 | Ceulemens |
| 9,603,815 | B2 | 3/2017 | Ceulemens |
| 9,610,260 | B2 | 4/2017 | Ceulemens |
| 10,351,509 | B2 | 7/2019 | Londesbrough |
| 10,351,510 | B2 | 7/2019 | Londesbrough |
| 10,452,815 | B2 | 10/2019 | Stewart et al. |
| 10,478,441 | B2 | 11/2019 | Ceulemens |
| 10,478,442 | B2 | 11/2019 | Ceulemens |
| 10,517,841 | B1 | 12/2019 | Galer et al. |
| 10,603,290 | B2 | 3/2020 | Farr |
| 10,682,317 | B2 | 6/2020 | Abu-Lzza |
| 10,689,324 | B2 | 6/2020 | Farr |
| 10,947,183 | B2 | 3/2021 | Londesbrough et al. |
| 10,950,331 | B2 | 3/2021 | Stewart et al. |
| 10,952,976 | B2 | 3/2021 | Galer |
| 11,040,018 | B2 | 6/2021 | Farr |
| 11,352,882 | B2 | 5/2022 | Farr |
| 2002/0038310 | A1 | 3/2002 | Reitberg |
| 2002/0098175 | A1 | 7/2002 | Zohoungbogbo |
| 2003/0007934 | A1 | 1/2003 | Rabinowitz et al. |
| 2003/0118654 | A1 | 5/2003 | Santos et al. |
| 2004/0249212 | A1 | 12/2004 | Smallridge et al. |
| 2005/0182103 | A1 | 8/2005 | Finke et al. |
| 2005/0260610 | A1 | 11/2005 | Kurtz et al. |
| 2006/0121066 | A1 | 6/2006 | Jaeger et al. |
| 2006/0270611 | A1 | 11/2006 | Dries et al. |
| 2008/0004904 | A1 | 1/2008 | Tran |
| 2008/0103179 | A1 | 5/2008 | Tam |
| 2008/0243584 | A1 | 10/2008 | Srinivasan |
| 2008/0261962 | A1 | 10/2008 | Greer |
| 2009/0171697 | A1 | 7/2009 | Glauser |
| 2010/0088778 | A1 | 4/2010 | Mulley |
| 2010/0298181 | A1 | 11/2010 | Hanada et al. |
| 2011/0092535 | A1 | 4/2011 | Barnes et al. |
| 2011/0212171 | A1 | 9/2011 | Venkatesh et al. |
| 2011/0230473 | A1 | 9/2011 | Gordon et al. |
| 2012/0065999 | A1 | 3/2012 | Takatoku |
| 2012/0107396 | A1 | 5/2012 | Khan |
| 2012/0115958 | A1 | 5/2012 | Mariotti et al. |
| 2012/0157392 | A1 | 6/2012 | Martin et al. |
| 2012/0270848 | A1 | 10/2012 | Mannion |
| 2012/0303388 | A1 | 11/2012 | Vishnubhatla |
| 2013/0218586 | A1 | 8/2013 | Huser |
| 2013/0296398 | A1 | 11/2013 | Whalley |
| 2014/0030343 | A1 | 1/2014 | Lamson |
| 2014/0142140 | A1 | 5/2014 | Bird |
| 2014/0162942 | A1 | 6/2014 | Ghosal |
| 2014/0329908 | A1 | 11/2014 | Ceulemens et al. |
| 2014/0343044 | A1 | 11/2014 | Ceulemens et al. |
| 2014/0343162 | A1 | 11/2014 | Ceulemens et al. |
| 2014/0348966 | A1 | 11/2014 | Balemba |
| 2015/0080377 | A1 | 3/2015 | Dhanoa |
| 2015/0291597 | A1 | 10/2015 | Mannion |
| 2015/0310187 | A1 | 10/2015 | Rabinowitz |
| 2015/0359755 | A1 | 12/2015 | Guy et al. |
| 2016/0136114 | A1 | 5/2016 | Ceulemens et al. |
| 2016/0228454 | A1 | 8/2016 | Zhang et al. |
| 2016/0249863 | A1 | 9/2016 | Ando |
| 2016/0279159 | A1 | 9/2016 | Hirano et al. |
| 2017/0020885 | A1 | 1/2017 | Hsu |
| 2017/0056344 | A1 | 3/2017 | Farr et al. |
| 2017/0071940 | A1 | 3/2017 | Osaleye et al. |
| 2017/0071949 | A1 | 3/2017 | De Witte et al. |
| 2017/0151194 | A1 | 6/2017 | Ceulemens |
| 2017/0151214 | A1 | 6/2017 | Ceulemens et al. |
| 2017/0151257 | A1 | 6/2017 | Ceulemens |
| 2017/0151259 | A1 | 6/2017 | Ceulemens |
| 2017/0174613 | A1 | 6/2017 | Londesbrough et al. |
| 2017/0174614 | A1 | 6/2017 | Farr et al. |
| 2017/0348303 | A1 | 12/2017 | Bosse |
| 2018/0028499 | A1 | 2/2018 | Baraban et al. |
| 2018/0055789 | A1 | 3/2018 | Farr |
| 2018/0092864 | A1 | 4/2018 | Martin et al. |
| 2018/0141953 | A1 | 5/2018 | Dax |
| 2018/0148403 | A1 | 5/2018 | Londesbrough et al. |
| 2018/0215701 | A1 | 8/2018 | Carroll et al. |
| 2018/0271821 | A1 | 9/2018 | Gold |
| 2018/0325909 | A1 | 11/2018 | DeWitte |
| 2019/0083425 | A1 | 3/2019 | Farr |
| 2019/0091173 | A1 | 3/2019 | Farfel |
| 2019/0091174 | A1 | 3/2019 | Galer |
| 2019/0091175 | A1 | 3/2019 | Morrison |
| 2019/0091176 | A1 | 3/2019 | Galer |
| 2019/0091177 | A1 | 3/2019 | Galer |
| 2019/0091179 | A1 | 3/2019 | Morrison |
| 2019/0125697 | A1 | 5/2019 | Farfel |
| 2019/0247333 | A1 | 8/2019 | Farfel |
| 2019/0380979 | A1 | 12/2019 | Galer |
| 2020/0030260 | A1 | 1/2020 | Sherrington et al. |
| 2020/0030341 | A1 | 1/2020 | Ceulemens |
| 2020/0170965 | A1 | 6/2020 | Boyd |
| 2020/0261380 | A1 | 8/2020 | Abu-Lzza |
| 2020/0276136 | A1 | 9/2020 | Galer |
| 2020/0297665 | A1 | 9/2020 | Martin |
| 2020/0306210 | A1 | 10/2020 | Morrison |
| 2020/0330406 | A1 | 10/2020 | Galer |
| 2021/0113495 | A1 | 4/2021 | Boyd |
| 2021/0121479 | A1 | 4/2021 | Ceulemens |
| 2021/0147335 | A1 | 5/2021 | Londesbrough |
| 2021/0158920 | A1 | 5/2021 | Stewart et al. |
| 2021/0267916 | A1 | 9/2021 | Farr |
| 2021/0299064 | A1 | 9/2021 | Morrison |
| 2021/0330610 | A1 | 10/2021 | Martin |
| 2021/0393550 | A1 | 12/2021 | Farr |
| 2021/0401776 | A1 | 12/2021 | Martin |
| 2022/0008389 | A1 | 1/2022 | Galer |
| 2022/0096514 | A1 | 3/2022 | Quan |
| 2022/0125743 | A1 | 4/2022 | Farr |
| 2022/0133652 | A1 | 5/2022 | Millet |
| 2022/0160727 | A1 | 5/2022 | Ceulemens |
| 2022/0193082 | A1 | 6/2022 | DeWitte et al. |
| 2022/0226262 | A1 | 7/2022 | Boyd et al. |

FOREIGN PATENT DOCUMENTS

| | | |
|---|---|---|
| CN | 103886415 | 6/2014 |
| CN | 111971035 | 11/2020 |
| DE | 2150399 | 4/1973 |

(56) References Cited

FOREIGN PATENT DOCUMENTS

| | | |
|---|---|---|
| EP | 0 441 160 | 8/1991 |
| EP | 0 920 864 | 6/1999 |
| EP | 1 399 015 | 1/2010 |
| EP | 2 399 513 | 12/2011 |
| EP | 3170807 | 5/2017 |
| GB | 1413078 | 7/1973 |
| GB | 1399015 | 6/1975 |
| GB | 1413070 | 11/1975 |
| GB | 2531282 | 4/2016 |
| HU | 204497 | 1/1992 |
| JP | A S64-066116 | 3/1989 |
| JP | H05-310564 A | 11/1993 |
| JP | A-2008-536545 | 9/2008 |
| JP | A-2009-525977 | 7/2009 |
| JP | A 2010-520162 | 6/2010 |
| JP | A-2011-221623 | 11/2011 |
| JP | A-2011-529923 | 12/2011 |
| JP | A-2012-511969 | 5/2012 |
| JP | A-2012-520130 | 9/2012 |
| JP | A-2012-208669 | 10/2012 |
| JP | A-2013-536857 | 9/2013 |
| JP | A-2013-248329 | 12/2013 |
| RU | 2317104 | 2/2008 |
| RU | 103209 | 3/2011 |
| RU | 2503448 | 1/2014 |
| RU | 2571501 | 12/2015 |
| WO | WO 1995/04713 | 2/1995 |
| WO | WO 1995/32962 | 12/1995 |
| WO | WO 2001/86506 | 11/2001 |
| WO | WO 2003/026591 | 4/2003 |
| WO | WO 2003/077847 | 9/2003 |
| WO | WO 2005/004865 | 1/2005 |
| WO | WO 2006/100676 | 9/2006 |
| WO | WO 2007/034476 | 3/2007 |
| WO | WO 2007/073503 | 6/2007 |
| WO | WO 2007/079181 | 7/2007 |
| WO | WO 2007/092469 | 8/2007 |
| WO | WO 2008/025148 | 3/2008 |
| WO | WO 2008/104524 | 9/2008 |
| WO | WO 2009/087351 | 7/2009 |
| WO | WO 2010/015029 | 2/2010 |
| WO | WO 2010/020585 | 2/2010 |
| WO | WO 2010/025931 | 3/2010 |
| WO | WO 2010/075115 | 7/2010 |
| WO | WO 2010/104841 | 9/2010 |
| WO | WO 2010/121022 | 10/2010 |
| WO | WO 2011/112606 | 9/2011 |
| WO | WO 2011/146850 | 11/2011 |
| WO | WO 2012/030927 | 3/2012 |
| WO | WO 2013/096878 | 6/2013 |
| WO | WO 2013/122897 | 8/2013 |
| WO | WO 2014/177676 | 11/2014 |
| WO | WO 2015/026849 | 2/2015 |
| WO | WO 2015/066344 | 5/2015 |
| WO | WO 2015/193668 | 12/2015 |
| WO | WO 2016/051271 | 4/2016 |
| WO | WO 2016/138138 | 9/2016 |
| WO | WO 2016/205671 | 12/2016 |
| WO | WO 2017/035267 | 3/2017 |
| WO | WO 2017/112702 | 6/2017 |
| WO | WO 2017/122701 | 6/2017 |
| WO | WO 2018/037306 | 3/2018 |
| WO | WO 2018/060732 | 4/2018 |
| WO | WO 2018/206924 | 11/2018 |
| WO | WO 2019/067405 | 4/2019 |
| WO | WO 2019/067413 | 4/2019 |
| WO | WO 2019/067419 | 4/2019 |
| WO | WO 2019/204593 | 10/2019 |
| WO | WO 2019/216919 | 11/2019 |
| WO | WO 2019/241005 | 12/2019 |
| WO | WO 2020/014075 | 1/2020 |
| WO | WO 2020/105005 | 5/2020 |
| WO | WO 2020/112460 | 6/2020 |
| WO | WO 2020/176276 | 9/2020 |
| WO | WO 2021/156437 | 8/2021 |
| WO | WO 2022/013425 | 1/2022 |
| WO | WO 2022/069489 | 4/2022 |

OTHER PUBLICATIONS

Aicardi et al., "Treatment of Self-Induced Photosensitive Epilepsy with Fenfluramine" New England Journal of Medicine (1985) 313:1419.

Aicardi et al., "Syncopal Attacks Compulsively Self-induced by Valsalva's Maneuver Associated with Typical Absence Seizures" Archives of Neurology (1988) 45:923-925.

Bird et al., "Combination of pharmaceutical compositions for treatment of neurological disorders" STN International (Columbus, Ohio) HCAPLUS database, Accession No. 2013:83254 (2013).

Coma et al., "New combination therapies for treating neurological dissorders" STN International (Columbus, Ohio) HCAPLUS database, Accession No. 2013:682383 (2013).

Cozzi et al., "Indan Analogs of Fenfluramine and Norfenfluramine Have Reduced Neurtoxic Potential" Pharmacology Biochemistry and Behavior (1998) 59(3):709-715.

Dimpfel et al., "Hesperidin and hesperetin for the treatment of epilepsy migraine, schizophrenia, depression, and drug abuse" STN International (Columbus, Ohio) HCAPLUS database, Accession No. 2006:1205690 (2006).

Droogmans et al., "Role of echocardiography in tox heart vavulopathy" European Journal of Echocardiography, 10:467-476 (2009).

Experimental Chemistry (Continued), Part 2, Separation and Purification, (Maruzen, Co., Ltd.), Jan. 25, 1967, pp. 159-162 and 184-193.

File History of U.S. Pat. No. 9,549,909 issued on Jan. 24, 2018 (571 pp).

File History of U.S. Pat. No. 9,603,815 issued on Mar. 28, 2017 (385 pp).

File History of U.S. Pat. No. 9,603,814 issued on Mar. 28, 2017 (466 pp).

File History of U.S. Pat. No. 9,610,260 issued on Apr. 4, 2017 (371 pp).

File History of U.S. Pat. No. 10,478,441 issued on Nov. 19, 2019 (761 pp).

File History of U.S. Pat. No. 10,478,442 issued on Nov. 19, 2019 (980 pp).

File History of U.S. Appl. No. 14/447,369, filed Jul. 30, 2014 (now abandoned) (285 pp.).

File History of U.S. Appl. No. 15/429,650, filed Feb. 10, 2017 (now abandoned) (267 pp).

File History of U.S. Appl. No. 15/429,641, filed Feb. 10, 2017 (now abandoned) (285 pp).

File History of U.S. Appl. No. 15/429,506, filed Feb. 10, 2017 (now abandoned) (641 pp).

File History of U.S. Appl. No. 16/596,166, filed Oct. 8, 2019 (now abandoned) (123 pp).

File History of U.S. Appl. No. 16/869,284, filed May 7, 2020 (now abandoned) (42 pp).

File History of U.S. Appl. No. 16/909,055, filed Jun. 12, 2020 (pending) (85 pp).

File History of U.S. Pat. No. 10,351,509 issued Jul. 16, 2019 (226 pp).

File History of U.S. Pat. No. 10,351,510 issued Jul. 16, 2019 (244 pp).

File History of U.S. Pat. No. 10,947,183 issued Mar. 16, 2021 (293 pp).

Garone et al., "Deoxypyrimidine monophosphate bypass therapy for thymidine kinase 2 deficiency" EMBO Molecular Medicine Aug. 1, 2014) 6(8):1016-1027.

Gross et al., "The influence of the sparteine/debrisoquine genetic polymorphism on the disposition of dexfenfluramine" Br J Clin Pharmacol (1996) 41:311-317.

Hattori et al., "A Screening test for the prediction of Dravet Syndrome before one year of age" Epilepsia (Apr. 2008) 49(4):626-633.

(56) References Cited

OTHER PUBLICATIONS

Hawkins et al., "Synthesis of [14C] Fenfluramine and [14C]-S780" Journal of Labelled Compounds (1974) 10(4):63-670.
Hirayama, Noriaki, Organic Compound Crystallization Handbook: Principles and Know-How (Maruzen, Co., Ltd.), Jul. 25, 2008, pp. 57-84.
Ji et al., "Study of Fenfluramine Synthesis Route" Journal of Shenyang College of Pharmacy (Apr. 1994) 11(2):116-118.
Kaiser et al., "Synthesis and Anorectic Activity o Some 1-Benzylcyclopropylamines" Journal of Medicinal Chemistry, American Chemical Society, US (1970) 13(5):820-826.
Lambert et al., "Inductive Enhancement of Aryl Participation" Journal of the American Chemical Society (Apr. 27, 1977) 99(9):3059-67.
Lewis et al., "Biosynthesis of Canescin, a Metabolite of *Aspergillus malignus*: Incorporation of Methionine, Acetate, Succinate, and Isocoumarin Precursors, Labelled with Deuterium and Carbon-13" J. Chem. Soc. Perkin Trans I (1988) pp. 747-754.
Lopinto-Khoury et al., "Antiepileptic Drugs and Markers of Vascular Risk" Curr Treat Options Neurol (Jul. 2010) 12(4):300-308.
Notification issued by the Director of Pharmaceutical and Medical Safety Bureau, Ministry of Health and Welfare, Guidelines for Residual Solvents in Pharmaceuticals, PMSB/ELD Notification No. 307, 1998, pp. 1-11.
Patani et al;, "Bioisosterism: A Rational Approach to Drug Design" Chem. Rev. (1996) 96:3147-3176.
Porra et al., "Determination of Fenfluramine Enantiomers in Pharmaceutical Formulations by Capillary Zone Electrophoresis" Chromatographia (Oct. 1995) 41(7/8):383-388.
Pottkamper et al., "The postictal state—What do we know?" Epilepsia (2020) 61 (6):1045-1061.
Registry(STN) [online], Jun. 7, 2015, [Retrieval Date: Sep. 28, 2020], CAS Registry No. 1775169-27-1.
Remi et al., "Clinical features of the postictal state: Correlation with seizure variables" Epilepsy & Behavior (2010) 91(2):114-117.
Su et al., "The Synthesis of 2-Amino-1-Penylpropanes" Chemical Journal of Chinese Universities (1988) 9(2):134-139.
Subota et al., "Signs and Symptoms of the postictal period in epilepsy: A systematic review and meta-analysis" Epilepsy & Behavior (2019) 94:243-251.
Thurman et al., "Sudden expected death in epilepsy: Assessing the public health burden" Epilepsia (2014) 55(10):1479-1485.
Tupal et al., "Serotonin 5-$HT_4$ receptors play a critical role in the action of fenfluramine to block seizure-induced sudden death in a mouse model of SUDEP" Epilepsy Research (2021) 177:1-7.
Van Der Steldt et al., "The Effect of Alkyl Substitution in Drugs" Arzneimittelforschung—Drug Research (1965) 15:1251-1253.
Vivero et al., "A close look at fenfluramine and dexfenfluramine" The Journal of Emergency Medicine (1998) 16(2):197-205.
Werbel et al., "Synthesis, Antimalarial Activity, and Quantitative Structure-Activity Relationships of Tebuquine and a Series of Related 5-[(7-Chloro-4-quinolinyl)amino]-3[(alkylamino)methyl] [1,1 '-biphenyl]-2-ols and N omega-Oxides" J. Med. Chem. (1986) 29:924-939.
Kelley et al., "Doose syndrome (myoclonic-astatic epilepsy): 40 years of progress" Developmental Medicine & Child Neurology (2010) 52(11):988-993.
McTague et al., "The genetic landscape of the epileptic encephalopathies of infancy and childhood" Lancet Neurol. (2016) 15:304-316.
Oguni et al., "Treatment and Long-Term Prognosis of Myoclonic-Astatic Epilepsy of Early Childhood ," Neuropediatrics (2002) 33(3):122-32.
Anandam, R., Affiliations Indian Journal of Pediatrics (Jan. 1, 2000) 67 (1 Suppl):S88-91 (Abstract Only).
Anonymous, "Determination That PONDIMIN (Fenfluramine Hydrochloride) Tablets, 20 Milligrams and 60 Milligrams, and PONDEREX (Fenfluramine Hydrochloride) Capsules, 20 Milligrams Were Withdrawn From Sale for Reasons of Safety or Effectiveness", Federal Register, (Sep. 29, 2015).
Anonymous, "MacReportMedia—Brabant Pharma Reports Two-Year Follow-up Data From a 19-year Observational Study Using Low-Dose Fenfluramine for the Treatment of Dravet Syndrome", Nov. 25, 2013 (Nov. 25, 2013).
Anonymous, "Health Technology Briefing: Fenfluramine hydrochloride for treatment of seizures associated with Lennox-Gastaut syndrome" NIHR Innovation Observatory (May 2019) 8 pages.
Anonymous "Selective Serotonin reuptake Inhibitor—Wikipedia" Internet https://en.wikipedia.org/wiki/Selective serotonin reuptake inhibitor (Feb. 1, 2020 (retrived on Feb. 4, 2020)).
Anonymous "Zogenix Announces Positive Top-Line Results from Global Pivotal Phase 3 Trial of FINTEPLA for the treatment of Lennox-Gastaut Syndrome" Bio Space (Feb. 6, 2020) pp. 1-12.
Aras et al., "The European patient with Dravet Syndrome: Results from a parent-reported survey on antiepileptic drug use in the European population with Dravet Syndrome" Epilepsy & Behavior (2015) 44:104-109.
Arzimanoglou, "Dravet syndrome: From electroclinical characteristics to molecular biology" Epilepsia, 50(Suppl. 8):3-9 (2009).
Baker, M. "Zogenix Completes Enrollment in Phase 3 Trial of FINTELPLA in Lennox-Gastaut Syndrome" (Jul. 8, 2019) 2 pages.
Boel and Casaer, "Add-on Therapy of Fenfluramine in Intractable Self-Induced Epilepsy" Neuropaediatrics 1996, 27(4):171-173.
F Brenot et al., "Primary Pulmonary Hypertension and Fenfluramine Use.", HEART, vol. 70, No. 6, Dec. 1, 1993 (Dec. 1, 1993), pp. 537-541.
Brunklaus et al., "Prognostic, clinical and demographic features in SCN1A mutation-positive Dravet syndrome" BRAIN, 2012, p. 1-8.
Brunklaus et al., "Dravet syndrome-From epileptic encephalopathy to channelopathy" Epilepsia (May 16, 2014) 55(7):979-984.
Buchanan, Gordon F. et al., Serotonin neurones have anti-convulsant effects and reduce seizure-induced mortality, The Journal of Physiology, 2014, vol. 592, Issue 19, p. 4395-4410.
Carvalho et al., "d-Amphetamine Interaction with Glutathione in Freshly Isolated Rat Hepatocytes" Chemical Research in Toxicology (Jan. 1996) 9(6):1031-1036.
Casaer et al., "Fenfluramine as a Potential Antiepileptic Drug" Epilepsia, 43(2), 205-206, 2002.
C. B. Catarino et al. "Dravet Syndrome as epileptic encephalopathy: Evidence from long-term course and neuropathology", Brain, vol. 134, No. 10 (Jun. 29, 2011) pp. 2982-3010.
Ceulemans et al., "Poster presented at the 69th Annual Meeting of the American Epilepsy Society" (Dec. 2015) Philadelphia.
Ceulemans et al., "Successful use of fenfluramine as an add-on treatment for Dravet syndrome" Epilepsia, 53(7), 2012, 1131-1139.
Ceulemans, "Overall management of patients with Dravet syndrome" Developmental Medicine & Child Neurology, 2011, 53, 19-23.
Ceulemans B. et al., "Successful use of Fenflurarmine as add-on treatment in Dravet syndrome: a two year prospective follow up", European Journal of Paediatric Neurology, vol. 17, 01101866, Sep. 1, 2013 (Sep. 1, 2013).
Ceulemans B., "Successful Use of Fenfluramine as Add-On Treatment in Dravet Syndrome" Epilepsia, 52(Suppl. 6):4-22 (2011).
Ceulemans et al., "Five-year extended follow-up status of 10 patients with Dravet syndrome treated with fenfluramine" Epilepsia (May 20, 2016) 57(7):e129-e134.
Chiron et. al., "The pharmacologic treatment of Dravet syndrome" Epilepsia (2011) 52(Suppl 2):72-75.
Clemens B., "Dopamine agonist treatment of self-induced pattern-sensitive epilepsy. A case Report" Epilepsy Res. 2. 1988, p. 340-343.
Clinical Trials ClinicalTrials.gov Identifier: NCT02224560 (Jul. 27, 2018).
Curzon et al., "Appetite suppression by commonly used drugs depends on 5-HT receptors but not on 5-HT availability" TIPS (1997) 18:21-25.
Devinsky et al., "Trial of Cannabidiol for Drug-Resistant Seizures in the Dravet Syndrome" The New Engalnd Journal of Medicine (May 25, 2017) 376(21):2011-2020.
C. Doege et al., "Myoclonic-astatic epilepsy: Doose-Syndrum 2014: Doose syndrome 2014", Zeitschrift FR Epileptologie, (Mar. 20, 2014).

(56) References Cited

OTHER PUBLICATIONS

Döring et al. "Thirty Years of Orphan Drug Legislation and the Development of Drugs to Treat Rare Seizure Conditions: A Cross Sectional Analysis" PLOS One, pp. 1-15 (Aug. 24, 2016).
Dravet, Charlotte, "The core Dravet syndrome phenotype" Epilepsia, 52(Supp. 2):3-9 (2011).
Faingold et al., "Prevention of seizure-induced sudden death in a chronic SUDEP model by semichronic administration of a selective serotonin reuptake inhibitor" Epilepsy & Behavior (2011) 22:186-190.
Favale et al., "The anticonvulsant effect of citalopram as indirect evidence of serotonergic impairment in human epileptogenesis" Seizure (2003) 12:316-319.
Franco-Perez, Javier "The Selective Serotonin Reuptake Inhibitors: Antidepressants with Anticonvulsant Effects?" Ann Depress Anxiety (2014) 1(5):1025 (2 pages).
Gastaut et al., "Compulsive respiratory sterotypies in children with autistic features: Polygraphic recording and treatment with fenfluramine" Journal of Autism and Developmental Disorders, (Sep. 1, 1987) 17(3):391-406.
K Gentsch et al., "Laboratory Research Fenfluramine Blocks Low-Mg2'-Induced Epileptiform Activity in Rat Entorhinal Cortex" Epilepsia, Jan. 1, 2000 (Jan. 1, 2000), pp. 925-928.
Gharedaghi et al., "The role of different serotonin receptor subtypes in seizure susceptibility" Exp. Brain Res (2014) 232:347-367.
Gioia et al., "Confirmatory Factor Analysis of the Behavior Rating Inventory of Executive Function (BRIEF) in a Clinical Sample" Child Neuropsychology (2002) 8(4):249-57.
Habibi et al., "The Impact of Psychoactive Drugs on Seizures and Antiepileptic Drugs" Current Neurology and Neuroscience Reports (Jun. 17, 2016) 16(8):1-10.
Haritos et al., "Metabolism of dexfenfluramine in human liver microsomes and by recombinant enzymes: Role of CYP2D6 and 1A2" Pharmcogenetics (Oct. 1998) 8(5):423-432.
Harvard Health Publishing, Harvard Medical School Generalized Seizures (Grand Mal Seizures) (Apr. 2014) pp. 1-5 (https://www.health.hearvard.edu/diseases-and-conditions/generalized-seizures-grand-mal-se . . .).
Hazai et al., "Reduction of toxic metabolite formation of acetaminophen" Biochemical and Biophysical Research Communications (Mar. 8, 2002) 291 (4):1089-1094.
Hegadoren et al., "Interactions of iprindole with fenfluramine metabolism in rat brain and liver" Journal of Psychiatry & Neuroscience (Mar. 1991) pp. 5-11.
Inoue et al., "Stiripentol open study in Japanese patients with Dravet Syndrome" Epilepsia, 50(11):2362-2368 (2009).
Isaac, Methvin, Serotonergic 5-HT2C Receptors as a Potential Therapeutic Target for the Design Antiepileptic Drugs, Current Topics in Medicinal Chemistry, 2005, vol. 5, Issue 1, p. 59-67.
Katholieke Universiteit Leuven, University Hospital Antwerp: "Interim results of a fenfluramine open-label extension study", European Patent Register (May 25, 2017).
Klein et al., "Cannabidiol potentiates Delta$^9$-tetrahydrocannabinol (THC) behavioural effects and alters THC pharmacokinetics during acute and chronic treatment in adolescent rats" Psychopharmacology (2011) 218:443-457.
Klein, M. T. and Teitler, M. , Distribution of 5-htlE receptors in the mammalian brain and cerebral vasculature: an immunohistochemical and pharmacological study, British Journal of Pharmacology, Jun. 2012, vol. 166, No. 4, p. 1290-1302.
Lagae et al. "A pilot, open-label study of the effectiveness and tolerability of low-dose ZX008 (fenfluramine HC1) in Lennox-Gastaut syndrome" Epilepsia (2018) 59: 1881-1888.
Leit, Silvana et al., Design and synthesis of tryptamine-based 5HT2C agonists for the treatment of certain CNS disorders, Division of Medicinal Chemistry Scientific Abstracts for the 240th National ACS Meeting and Exposition, Jul. 28, 2010, MEDI367.
Lejeune et al., "Psychometric Support for an Abbreviated Version of the Behavior Rating Inventory of Executive Function (BRIEF) Parent Form" Child Neuropsychology (2010 16:182-201.
Lopez-Meraz et al., "5-$HT_{1A}$ receptor agonist modify epileptic seizures in three experimental models in rats" Neuropharmacology (2005) 49:367-375.
Manzke et al., "5-HT4(a) receptors avert opiod-induced breathing depression without loss of analgesia" Science (Jul. 11, 2003) 301:226-229.
Martin, et al., "An Examination of the Mechanism of Action of Fenfluramine in Dravet Syndrome: A Look Beyond Serotonin" Presented as part of the Zogenix Scientific Exhibit During the 70$^{th}$ Annual Meeting of the American Epilepsy Society, Houston, Texas (Dec. 2-6, 2016).
Meador K J., "Seizure reduction with fluoxetin in an adult woman with Dravet syndrome", Epilepsy & Behavior Case Reports, Elsevier BV, NL, vol. 2, Jan. 1, 2014 (Jan. 1, 2014), pp. 54-56.
Mudigoudar et al., "Emerging Antiepileptic Drugs for Severe Pediatric Epilepsies" Seminars in Pediatric Neurology (Jun. 2016) 23(2):167-179.
Mulley et al., "SCN1A Mutations and Epilepsy" Human Mutation (2005) 25:535-542.
Naithani et al., "The Conventional Antiepileptic Drug Use When Compared to a Combination Therapy Regime in a Teaching Hospital in India" International Journal of Pharma and Bio Sciences (2012) 3(1):B-191-B-197.
NCT02682927 (Sep. 3, 2016, 10 pages) Accessed from https://www.clinicaltrials.gov/ct2/history/NCT02682927?V=Vlew#StudyPageTop on Mar. 18, 2019).
Nozulak et al., "(+)-cis-4,5,7a,8,9,10,11,11 a-Octahydro-7H-10-methylindolo[1,7-bc][2,6]-naphthridine: A 5-$HT_{2C/2B}$ Receptor Antagonist with Low 5-$HT_{2A}$ Receptor Affinity" J. Med. Chem. (1995) 38:28-33.
O'Neill et al., "GR46611 potentiates 5-$HT_{1A}$ receptor-mediated locomotor activity in the guinea pig" European Journal of Pharmacology (1999) 370:85-92.
ONFI Prescribing Information. Lundbeck, Deerfield, Reference ID: 4028780 [online], Dec. 2016, [retrieved on Jun. 22, 2021, <URL: https://www.accessdata.fda.gov/drugsatfda_docs/label/2016/203993s005lbl.pdf>.
Pirincci et al., "The Effects of Fefluramine on Blood and Tissue Seratonin (5-Hydroxytryptamine) Levels in Rats" Turk J Vet Anim Sci (2005) 29:857-863.
Pittala, Valeria et al., 5-HT7 Receptor Ligands: Recent Developments and Potential Therapeutic Applications, Mini-Reviews in Medicinal Chemistry, 2007, vol. 7, Issue 9, p. 945-960.
Jake Remaly: "Fenfluramine Reduces Convulsive Seizure Frequency in Dravet Syndrome. Epilepsy Resource Center", Jan. 1, 2018 (Jan. 1, 2018).
Remington, "The Science and Practice of Pharmacy", Nineteenth Edition (1995), pp. 710-712.
Rho, Jong M. "Basic Science Behind the Catastrophic Epilepsies" Epilepsia (2004) 45(Suppl.5):5-11.
Rothman et al., "Serotonergic drugs and valvular heart disease" Expert Opinion on Drug Safety (May 2009) 8(3):317-329.
Russo et al., "Agonistic Properties of Cannabidiol at 5-HT1a Receptors" Neurochemical Research (2005) 30(8):1037-1043.
Schoonjans, An-Sofie "Low-dose fenfluramine in the treatment of neurologic disorders: experience in Dravet syndrome" Therapeutic Advances in Neurological Disorders (Jan. 1, 2015) pp. 328-338.
Schoonjans et al. "Low-dose fenfluramine significantly reduces seizure frequency in Dravet syndrome: a prospective study of a new cohort of patients", European Journal of Neurology, vol. 24, No. 2, (Oct. 28, 2016), pp. 309-314.
An-Sofie Schoonjans et al.: "Cardiovascular Safety of Low-Dose Fenfluramine in Dravet Syndrome: A Review of its Benefit-Risk Profile in a New Patient Population", Current Medical Research and Opinion, vol. 33, No. 10, Jul. 31, 2017 (Jul. 31, 2017), pp. 1773-1781.
Selmer et al., "SCN1A mutation screening in adult patients with Lenox-Gastaut syndrome features" Epilepsy & Behavior (Nov. 1, 2009) 16(3):555-57.
Sharma et al. Indian Journal of Pharmacology, 1996, 28(1), 1-10.
Slick et al., "Frequency of Scale Elevations and Factor Structure of the Behavior Rating Inventory of Executive Function (Brief) in

(56) References Cited

OTHER PUBLICATIONS

Children and Adolescents with Intractiable Epilepsy" Child Neuropsychology (2006) 12:181-189.
Sourbron et al., "Serotonergic Modulation as Effective Treatment for Dravet Syndrome in Zebrafish Mutant Model" ACS Chemical Neuroscience (Feb. 17, 2016) 7(5):588-598.
Study NCT02926898 on Date: May 1, 2017 (v6), ClinicalTrials.gov archive[online], May 1, 2017, [retrieved on Jun. 22, 2021 ], <URL: https://clinicaltrials.gov/ct2/history/NCT02926898>.
Sullivan et al. "Effext of ZX008 (fenfluramine HC1 oral solution) on total seizures in Dravet syndrome" Neurology: Official Journal of the American Academy of Neurology, 2018, 90(24):e2187-e2811.
Van Rijckevorsel, Kenou, "Treatment of Lennox-Gastaut syndrome: overview and recent findings" Neuropsychiatric Disease and Treatment, 4(6):1001-1019 (2008).
Vela, Jose Miguel "Repurposing Sigma-1 Receptor Ligands for COVID-19 Therapy?" Frontiers in Pharmacology (Nov. 2020) pp. 1-23.
Vickers et al., "Oral Administration of the 5-HT2C receptor agonist, mCPP, reduces body weight gain in rats over 28 days as a result of maintained hypophagia" Psychopharmacology (May 2003), 167 (3): 274-280.
Viola et al., "The Behavior Rating Inventory of Executive Function (BRIEF) to Identify Pediatric Acute Lymphoblastic Leukemia (ALL) Survivors At Risk for Neurocognitive Impairment" Journal of Pediatric Hematology/Oncology (Apr. 1, 2017) 39(3):174-178.
Wallace et al., "Pharmacotherapy for Dravet Syndrome" Paediatr. Drugs, 18(3):197-208 (Jun. 2016).
Wirrell et al., "Stiripentol in Dravet syndrome: Results of a retrospective U.S. study" Epilepsia (2013) 54(9):1595-1604.
Wirrell et al., "Stiripentol in Dravet Syndrome: Is it Worth It?" Epilepsy Currents, 14(1):22-23 (Jan./Feb. 2014).
Wirrell et al., "Treatment of Dravet Syndrome" Can. J. Neurol. Sci., 43(Suppl. 3):S13-18 (Jun. 2016).
Wirrell et al., "Optimizing the Diagnosis and Management of Dravet Syndrome: Recommendations From a North American Consensus Panel" Pediatric Neurology (Mar. 2017) 68:18-34.
Wurtman et al., "Fenfluramine and other serotoninergic drugs depress food intake and carbohydrate consumption while sparing protein consumption" Current Medical Research and Opinion (1979) 6(1 Supp):28-33.
Yamaori et al., "Potent inhibition of human cytochrome P450 3A isoforms by cannabidiol: Role of phenolic hydroxyl groups in the resorcinol moiety" Life Sciences (2011)88:730-736.
Yoshida et al. (2017), "Impact of Physiologically Based Pharmacokinetic Models on Regulatory Reviews and Product Labels: Frequent Utilization in the Field of Oncology" in Clinical Pharmacology and Therapeutics 2017; 101(5): 597-602.
Zaccara et al., "Interactions between antiepileptic drugs, and between antiepileptic drugs and other drugs" Seminar in Epileptology (2014) 16(4):409-432.
Zhang et al., *A Physiological-based Pharmacokinetic (PBP) Modeling Approach to Quantifying Drug-Drug Interactions: Applications to the Development of Fenfluramine (ZX008) for Treatment of Seizures in Dravet Syndrome (DS)*. Presented at the 2016 American Conference for Pharmacokinetics.
Zhang et al., A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS). Published in Abstracts accepted for American Conference on Pharmacometrics 2016 (ACoP7).
Zhang et al., "Pharmacological Characterization of an Antisense Knockdown Zebrafish Model of Dravet Syndrome: Inhibition of Epileptic Seizures by the Serotonin Agonist Fenfluramine" PLOS ONE (May 12, 2015) 10(5)::16-17 (Abstract).
Zhuang et al. (2016), "PBPK modeling and simulation in drug research and development" in Acta Pharmaceutica Sinica B 2016;6(5):430-440.
Zogenix "Corporate Update Nasdaq: ZGNX" (Jun. 1, 2016) Retrieved from the Internet: URL:http://www.jefferies.com/CMSFiles/Jefferies.com/files/Conferences/060716/Presentations/Zogenix%20Inc.pclf[retrieved on Feb. 21, 2018].
Bagdy et al., "Serotonin and epilepsy," J. Neurochem., 100:857-73 (2007).
Ceulemans et al., "Clinical Correlations of Mutations in the SCN1A Gene: From Febrile Seizures to Severe Myoclonic Epilepsy in Infancy" Pediatr. Neurol. 30(4):236-43 (2004).
Coleman et al., "Monitoring for adverse drug reactions," Br. J. Clin. Pharmacol., 61(4):371-78 (2006).
"Diacomit: EPAR—Scientific Discussion," European Medicines Agency ("EPAR Diacomit") https://www/ema/europa.eu/en/documents/scientific-discussion/dlacomit-epar-scientific-discussion_en.pdf, published 2009.
Ferretti et al., "Direct High-performance liquid chromatograph resolution on a chiral column of dexfenfluramine and its impurities, in bulk raw drug and pharmaceutical formulations" J. Chromatogr. A. 731:340-45 (1996).
Gordon et al., "A SARS-CoV-2 protection interaction map reveals targets for drug repurposing" Nature (Apr. 30, 2020) 583(7816:459-468.
Haute Autoritéde Santé(HAS), French National Authority for Health, issued an opinion on Diacomit ("HAS Opinion") https://www.has-sante.fr/upload/dox/application/pdf/2010-01/diacomit_ct_4347.pdf(Jun. 6, 2007) .
Heisler et al., "Epilepsy and Obesity in Serotonin 5-$HT_{2C}$ Receptor Mutant Mice," Ann. NY Acad. Sci. 861:74-78 (1998).
International Conference On Harmonisation Of Technical Requirements for Registration of Pharmaceuticals for Human Use, "ICH Harmonised Tripartite Guidline: Impurities in New Drug Substances," Q3A(R2) (2006).
Jingyu et al., "Study on Synthesis of Amphetamine Compounds" Chern J. of Chinese Univ., 9(2), 12 pages (1988).
Martin et al., "Fenfluramine acts as a positive modulator of sigma-1 receptors" Epilepsy and Behavior, Academic Press, San Diego, CA, US (Mar. 10, 2020) 105:1-9.
Mathews et al., "Effect of D-Fenfluramine on the Lymphocyte Response of HIV+ Humans" International Journal of Immunopharmacology (Jan. 1, 1998) 20:751-763.
Olson et al., "Cyclin-Dependent Kinase-Like 5 Deficiency Disorder: Clinical Review" Pediatric Neurology (2019) 97:18-25.
Public Law 110-85, $110^{th}$ Congress ("FDA Amendments Act of 2007") published 2007.
Rothman et al., "(+)-Fenfluramine and Its Major Metabolite, (+)-Norfenfluramine, Are Potent Substrates for Norepinephrine Transporters," J. Pharmacol. Exp. Ther., 305(3):1191-99 (2003).
Scala et al., "CDKL5/STK9 is mutated in Rett syndrome variant with infantile spasms" J Med Genet (2005) 42:103-107.
Tran et al., "Dakin-West Synthesis of β-Aryl Ketones" J. Org. Chem. (2006) 71:6640-6643.
Wee et al., "Risk for Valvular Heart Disease among Users of Fenfluramine and Dexfenfluramine Who Underwent Echocardiography before Use of Medication," Annals of Internal Medicine, 129(11):870-874 (1998).
Asatryan, Babken "Challenges in Decoding Sudden Unexpected Death in Epilepsy: The Intersection Between Heart and Brain in Epilepsy" Journal of the American Heart Association (2021) 10(23):e023571, pp. 1-4.
BNF 39—British National Formulary (Mar. 2000) p. 197.
Caraballo et al., "Ketogenic diet in patients with Lennox-Gastaut syndrome" Seizure (2014) 23:751-755.
Cross et al., "Expert Opinion on the Management of Lennox-Gastaut Syndrome: Treatment Algorithms and Practical Considerations" Frontiers in Neurology (Sep. 29, 2017) 8(505):1-18.
Fisher et al., "Definition of the postictal state: When does it start and End?" Epilepsy & Behavior (2010) 19(2):100-104.
Grosso et al., "Dexfenfluramine effective in drug-resistant temporal lobe epilepsy" Neurology, Lippincott Williams & Wilkins, Philadelphia, US (Sep. 25, 2001) 57(6):1139-1140.
Hay et al., "Clinical development success rates for investigational drugs" Nature Biotechnology (Jan. 2014) 32(1):40-51.

(56) References Cited

OTHER PUBLICATIONS

Knupp et al., "Efficacy and Safety of Fenfluramine for the Treatment of Seizures Associated with Lennox-Gastaut Syndrome" JAMA Neurology (Jun. 2022) 79(6):554-564.
MIMS—Monthly Index of Medical Specialties (Sep. 1997) pp. 240-241.
Samanta, Debopam "Changing Landscape of Dravet Syndrome Management: An Overview" Neuropediatrics (2020) 51(2):135-145.
Archer et al., "Primary Pulmonary Hypertension, A Vascular Biology and Translational Research "Work in Progress"" Clinical Cardiology: New Frontiers, Circulation, 102:2781-2791 (Nov. 28, 2000).
Echocardiogram, Echocardiogram Test for Pulmonary Arterial Hypertension PAH (https://pulmonaryhypertensionm.com/echocardiogram/) pp. 1-5 (Jan. 4, 2012).
FDA-approved Treatments for Pulmonary Hypertension, Vera Moulton Wall Center for Pulmonary Vascular Diseases, Stanford (https://med.stanford.edu/wallcenter/patient-resources/fda.html) pp. 1-8 (Jan. 19, 2017).
Gardner, Amanda "Living Your Best With Pulmonary Hypertension" WebMD, pp. 1-5 (Jan. 2, 2019).
Khan et al., "Epileptic Encephalopathies: An Overview"Epilepsy Research and Treatment, vol. 2012, pp. 1-8 (Sep. 12, 2012).
Mari et al., "CDKL5 belongs to the same molecular pathway of MeCP2 and it is responsible for the early-onset seizure variant of Rett syndrome" Human Molecular Genetics (2005) 14(14):1935-1946.
Pulmonary Hypertension and Edema, (pulmonaryhypertensionnews.com/pulmonary-hypertension-and-edema/) pp. 1-3 (Nov. 9, 2015).
Scheffer et al., "ILAE classification of the epilepsies: Position paper of the ILAE Commission for Classification and Terminology" Epilepsia (2017) 58)4):512-521.
Specchio et al., "International League Against Epilepsy classification and definition of epilepsy syndromes with onset in childhood: Position paper by the ILAE Task Force on Nosology and Definitions" Epilepsia (Mar. 17, 2022) 00:1-45.
Weir et al., "Anorexic Agents Aminorex, Fenfluramine, and Dexfenfluramine Inhibit Potassium Current in Rat Pulmonary Vascular Smooth Muscle and Cause Pulmonary Vasoconstriction" American Heart Association, Circulation, 94(9):2216-2220 (Nov. 1996).
Zuberi et al., "Commentary: A New Classification is Born" International League Against Epilepsy (2017) pp. 511.
Aylward et al., "Screening and Assessment Tools" Developmental-Behavioral Pediatrics Evidence and Practice (2008) 123-201.
Berge et al., "Pharmaceutical Salts" J. Pharm Sci (1977) 68(1):1-19.
Busner et al., "Global Impressions Scale: Applying a Research Tool in Clinical Practice" Psychiatry (2007) 29-37.
Ceulemans B., "Successful Use of Fenfluramine as Add-On Treatment in Dravet Syndrome" Epilepsia, 52(Suppl. 6):4-22 (2011) (Abstract Only).
De Jonghe et al., "Molecular genetics of Dravet syndrome" Developmental Medicine & Child Neurology (2011) 53 (Supp 2):7-10.
Dravet. Charlotte, "Dravet Syndrome History" Developmental Medicine & Child Neurology (2011) 53 (Suppl. 2):1-6.
"Guideline on clinical investigation of medicinal products in the treatment of epileptic disorders" European Medicines Agency (Jul. 22, 2010) pp. 1-17.
Marini et al., "The genetics of Dravet Syndrome" Epilepsia (2011) 52(Suppl. 2):24-29.
Mayer et al., "Refractory Status Epilepticus" Archives of Neurology, American Medial Association, Chicago, IL, US (Feb. 1, 2022) 59(2):205-210.
Patino et al., "A Functional Null Mutation of SCN1B in a Patient with Dravet Syndrome" J. Neurosci. (2009) 29(34):10764-10778.
Rawson et al., "Bacterial and Funcal Coinfection in Individuals with Coronavirus: A Rapid Review to Support COVID-19 Antimicrobial Prescribing" Clinical Infection Diseases (2020) 71:2459-2468.
Shorvon et al., "The treatment of super-refractory status epilepticus: a critical review of available therapies and a clinical treatment protocol" Brain (Oct. 1, 2011) 134(10)2802-2818.
Singh et al., "A Role of SCN9A in Human Epilepsies, As a Cause of Febrile Seizures and As a Potential Modifier of Dravet Syndrome" PLoS Genetics (2009) 5(9):9-12 (pp. 1-14).
WIKIPEDIA "Marburg acute multiple sclerosis" (Dec. 26, 2020), retrieved on Oct. 9, 2022.

* cited by examiner

METHOD OF TREATING PATIENTS INFECTED WITH SEVERE ACUTE RESPIRATORY SYNDROME CORONAVIRUS 2 (SARS-COV-2)

CROSS REFERENCE TO RELATED APPLICATIONS

This application claims priority to U.S. Provisional Applications 63/053,162, filed Jul. 17, 2020; 63/054,397, filed Jul. 21, 2020; and 63/058,334, filed Jul. 29, 2020, which are incorporated herein by reference.

FIELD OF THE INVENTION

A method of treating patients infected with severe acute respiratory syndrome coronavirus 2 (SARS-CoV-2) which leads to COVID-19 disease is described whereby the patient is repeatedly treated with fenfluramine and the treatment continued to obtain a desired end point not previously recognized.

BACKGROUND OF THE INVENTION

The free base of fenfluramine is an amphetamine derivative having the structure:

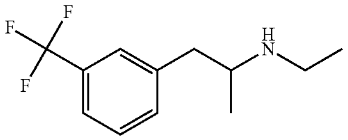 [SMILES: CCNC(C)Cc1cccc(C(F)(F)F)c1]

Structure 1

Free Base of Fenfluramine (RS)—N-ethyl-1-[3-(trifluoromethyl)phenyl]propan-2-amine As used herein, the term “fenfluramine” refers to both the free base depicted in Structure 1 and its pharmaceutically acceptable salts thereof.

Fenfluramine was first marketed in the US in 1973 and had been administered in combination with phentermine to prevent and treat obesity. However, in 1997, it was withdrawn from the US market as its use was associated with the onset of cardiac valvular fibrosis and pulmonary hypertension. Subsequently, the drug was withdrawn from sale globally and is no longer indicated for use in any therapeutic area anywhere in the world.

Despite the health concerns surrounding fenfluramine, attempts have been made to identify further therapeutic uses for that product. Aicardi and Gastaut (New England Journal of Medicine (1985), 313:1419 and Archives of Neurology (1988) 45:923-925) reported four cases of self-induced photosensitive seizures that responded to treatment with fenfluramine. Clemens, in Epilepsy Research (1988) 2:340-343 reported a study on a boy suffering pattern sensitivity-induced seizure that were resistant to anticonvulsive treatment. Fenfluramine reportedly successfully terminated these self-induced seizures and the author concluded that this was because fenfluramine blocked the photosensitive triggering mechanism.

SUMMARY OF THE INVENTION

Provided is a method of treating a patient infected with severe acute respiratory syndrome coronavirus 2 (SARS-CoV-2), comprising: determining the patient has been infected with SARS-CoV-2; and administering to the patient a therapeutically effective dose of fenfluramine.

In an aspect of the invention, the fenfluramine is the sole therapeutic agent administered to the patient.

In another aspect of the invention, the fenfluramine is adjunctive therapy and is co-administered with a second, or a second and third, or a second, third and fourth, therapeutic agent. Any second, or any combination of second and third, or any combination of second, third and fourth therapeutic agents of interest may be utilized. In some cases, the second, or a second and third, or a second, third and fourth, therapeutic agent is selected from the group consisting of: Remdesivir, a monoclonal antibody, convalescent plasma from a subject who had previously been infected with SARS-CoV-2 and which comprises antibodies for SARS-CoV-2, a viricide, amantadine, rimantadine, and a nucleoside analog. Exemplary nucleoside analogs include acyclovir and zidovudine (AZT). In some cases, the co-therapeutic agent is zinc.

In another aspect of the invention, the treatment continues in amounts and over a period of time so as to reduce the need by the patient for antiviral medication by 25% or more, 50% or more, 75% or more, or completely eliminate the need for antiviral medication.

In another aspect of the invention, the treatment is continued in amounts and over a period of time so as to reduce the patient’s hospitalization visits by 25% or more, 50% or more, 75% or more, or completely eliminate hospitalization visits due to infection with severe acute respiratory syndrome coronavirus 2 (SARS-CoV-2) which leads to COVID-19 disease.

Another aspect of the invention comprises administering a liquid fenfluramine formulation by the use of an oral syringe which is graduated for precise measurement of the liquid formulation. The formulation may include flavoring and coloring agents or may be completely devoid of any excipient materials beyond those necessary to dissolve the fenfluramine in the liquid which may be water.

In some cases, the fenfluramine can be administered directly to a lung of the patient. For instance, an aqueous composition comprising fenfluramine can be aerosolized to generate an aerosol, and the aerosol can be directed into a lung of the patient. In some cases, the aerosol comprises liquid droplets of the aqueous fenfluramine composition having a dimension (e.g. a diameter) of 10 μm or less, such as 1 μm or less or 0.1 μm or less. In some cases the administering comprises directing an aerosol comprising fenfluramine into a lung of the patient.

In some cases, the administering includes delivering the dose of fenfluramine to the patient as an aerosol. In other words, an aqueous fenfluramine solution is aerosolized and then directed to the nose or lungs of the subject.

DETAILED DESCRIPTION OF THE INVENTION

Figure 1A:
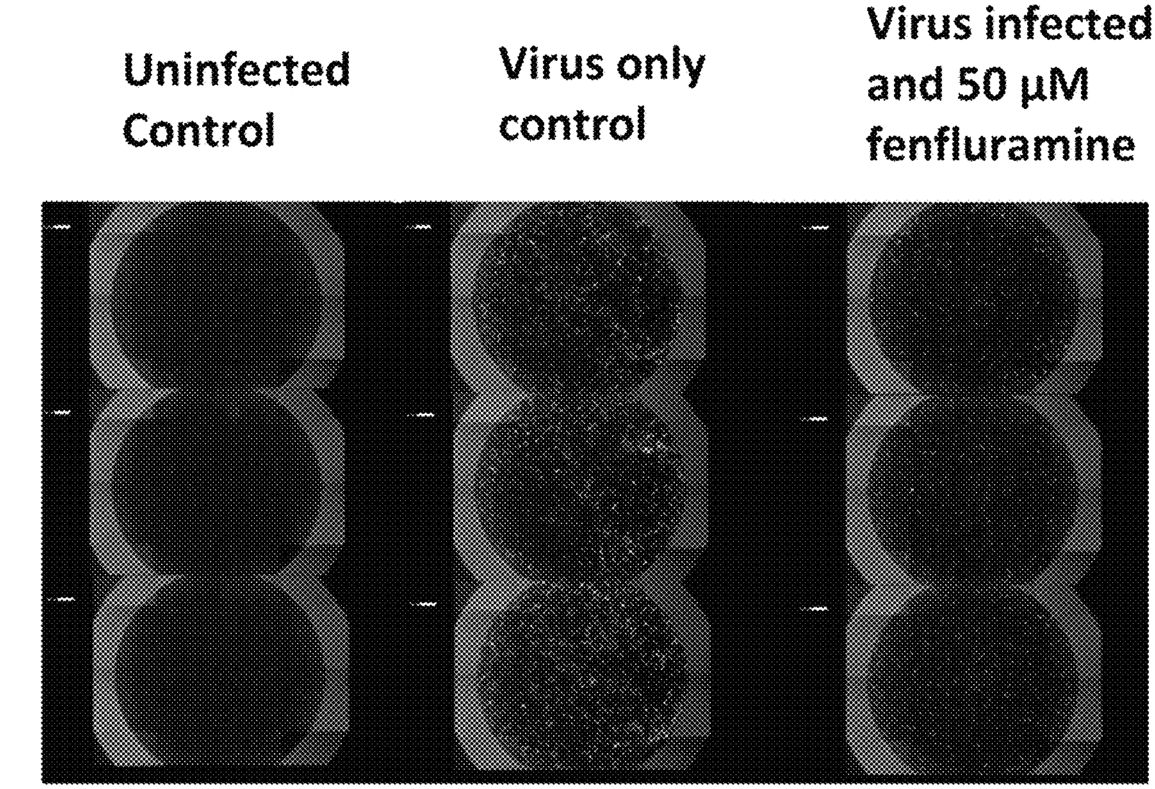
FIG. 1A shows viral replication measured by quantification of mNeonGreen fluorescence of the SARS-CoV-2 reporter virus in infected Calu-3 cells in the presence and absence of Compound A treatment (50 mM). Multiplicity of infection=0.5. 1A. images of infected and controls wells.

Before the present methods of treatment are described, it is to be understood that this invention is not limited to particular method described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a step of administering" includes a plurality of such steps and reference to "the symptom" includes reference to one or more symptoms and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention.

Further, the dates of publication provided may be different from the actual publication dates which may need to be independently confirmed.

Definitions

The term "fenfluramine" refers to both the free base depicted in Structure 1 and its pharmaceutically acceptable salts thereof. Pharmaceutically acceptable acid addition salts are those formed from acids which form non-toxic acid anions such as, for example, the hydrochloride, hydrobromide, sulphate, phosphate or acid phosphate, acetate, maleate, fumarate, lactate, tartrate, citrate and gluconate salts.

Fenfluramine was first approved in 1976 as an anoretic agent. The mechanism of action of fenfluramine in promoting weight loss during the 1970's and 1980's was unclear, but thought to be related to brain levels (or turnover rates) of serotonin or to increased glucose utilization. The anti-appetite effects of fenfluramine have been shown to be suppressed by serotonin-blocking drugs and by drugs that lower brain levels of this amine neurotransmitter. Furthermore, decreased serotonin levels produced by selective brain lesions have been shown to suppress the action of fenfluramine. Fenfluramine was approved for use in the treatment of Dravet Syndrome, a childhood epileptic encephalopathy, in June 2020 Additional research done on the mechanism of action of fenfluramine has demonstrated interference with serotonin synaptic reuptake and triggering the release of serotonin in the brain due to disruption of its vesicular storage.

The effects of dexfenfluramine (d-Fen, the d-enantiomer component of racemic fenfluramine) on lymphocytes in HIV+ and HIV-comparators. It was found that dexfenfluramine increased the amount of the cytokine IL-2 produced by CD4+ and CD8+ lymphocytes from HIV+ patients. d-FEN increased the number of CD4+ and CD8+ lymphocytes that produced IFN-gamma from either HIV+ or HIV-patients and increased the number of HIV+ patient's CD8+ lymphocytes that produce TNF-alpha [Int J Immunopharmacol.; 20(12):751-63 (December 1998)].

Data from even more recent studies provide evidence that fenfluramine is a positive allosteric modulator of the sigma-1 receptor. [P. Martin, et al., Poster 2.032; 71st Annual Meeting of the American Epilepsy Society, Dec. 1-5, 2017, Washington, D.C.]. The Sigma-1 receptor (S1R) protein, which serves as a molecular chaperone and functional modulator, is involved in restoring homeostasis and modulation of many biological mechanism associated with neurodegeneration. Thus sigma-1 agonists are useful in providing neuroprotection and restoration and maintenance of neuronal signaling pathways. Methods of using fenfluramine in a method for improving cognition and slowing or halting cognitive decline have been disclosed in WO2020105005. Studies combining low doses of fenfluramine or (+)-fenfluramine and PRE-084 (a sigma-1 agonist) followed by calculation of combination indexes (Maurice, 2016) showed that most combinations led to synergistic effects in several animal models. Racemic fenfluramine, as well as its active isomer (+)-fenfluramine, behaved in vitro and in vivo as Sig1R positive modulators. [Maurine, T., et al., Soc. Neurosci. Abstr. 692]

US201916360375 to Fekete and Vannay describes the use of sigma-1 ligands in methods of lessening or preventing tissue scarring including lung fibrosis. Sigma-1 receptor plays an important role in the functioning of tissues associated with the endocrine, immune and nervous systems.

The terms "cytokine release syndrome" (CRS) and "cytokine storm" are used interchangeably herein to describe exaggerated, excessive synthesis of certain cytokines such as IL-6 in response to any type of stress/trauma including infection with a pathogen, chemical exposure and physical trauma. The term is used to refer to the result of infection known to be capable of producing CRS. The stress may be a stress induced by viral infection and more particularly viral infection caused by infection with any virus, including COVID-19 which can produce CRS. The cytokine level is exaggerated or excessive when it reaches a level which is no longer beneficial. Such a level may generate a systemic inflammatory response syndrome including sepsis, macrophage activation syndrome and hemophagocytic, lymphohistiocytosis. These responses can result in a range of undesirable results including organ failure and death.

Two viral entry points were identified in April 2020 after researchers demonstrated that SARS-CoV-2 uses the SARS-CoV receptor ACE2 for entry and the serine protease TMPRSS2 for S protein priming. [Hoffmann, M., et al., Cell; 181(2):271-280. (2020.] More recently, in vitro infectivity assays in Vero 6 cells have highlighted sigma receptors land 2 in the endoplasmic reticulum as two (among several other receptor targets) as potential candidates for drug development to combat SARS-CoV-2 after demonstrating that sigma 1 and sigma 2 receptors are "hijacked" by SARS-CoV-2 proteins, Nsp6 and ORF9c, respectively. [Nature Biotechnology Vol. 38 p. 655-664 (June 2020)]. The sigma 1 receptor, which carries out Ca2+ signaling in the endoplasmic reticulum's mitochondria-associated membrane, is known to promote cell survival, activate the unfolded protein response, mediate lipid remodeling and influence autophagosome-lysosome fusion. Three generic drugs, hydroxy-chloroquine, haloperidol and clemastine were tested and shown to inhibit SARS-CoV-2 in vitro through this mechanism.

Haloperidol binds in the low nM range to both sigma-1 and sigma-2 receptors. Chloroquine, which is currently in clinical trials for COVID-19 has mid-nM activity at the Sigma1 receptor, and low uM activity against the Sigma2 receptor. Fenfluramine has been reported to have a Ki of 266 nM in a non-selective sigma binding assay. [Martin, P., et al., Epilepsy & Behavior 105 (2020) 106989; //doi.org/10.1016/j.yebeh.2020.106989]

Additionally, reduction of the level of Sigma-1 receptors in human cells has recently been shown to slow or prevent SARS-CoV-2 viral replication in human cells and sigma-2 receptor (also referred to as TMEM97; https://www.uniprot.org/uniprot/Q5BJF2), has also be implicated in SARS-CoV-2 infection and is an endoplasmic reticulum-resident transmembrane protein that regulates the sterol transporter NPC1 [Alon, A., et al., Proc. Natl. Acad. Sci. U.S.A. 114:7160-7165 (2017)]

The term "ZX008" refers to fenfluramine hydrochloride formulated as an oral solution.

The term "reduction from baseline" is used throughout in order to refer to a reduction relative to the same or similar patient prior to administration of fenfluramine. During the baseline period, the patient is treated with other therapeutic agents, except for fenfluramine. Treatment with the same other therapeutic agents is substantially maintained during the treatment with fenfluramine. The comparison is made relative to the observations, measurements or tests made during the baseline period.

The term metered-dose inhaler (MDI) is a device that delivers a specific amount of medication such as a formulation of fenfluramine to the lungs, in the form of a short burst of aerosolized medicine that is usually self-administered by the patient via inhalation. It is the most commonly used delivery system for treating asthma, chronic obstructive pulmonary disease (COPD) and other respiratory diseases. The fenfluramine medication could be administered via a metered dose inhaler along with a bronchodilator, corticosteroid or a combination of both.

A metered-dose inhaler consists of three major components; the canister which is produced in aluminum or stainless steel by means of deep drawing, where the formulation resides; the metering valve, which allows a metered quantity of the formulation to be dispensed with each actuation; and an actuator (or mouthpiece) which allows the patient to operate the device and directs the aerosol into the patient's lungs. The formulation itself is made up of the fenfluramine drug, a liquefied gas propellant and, in many cases, stabilizing excipients. The actuator contains the mating discharge nozzle and generally includes a dust cap to prevent contamination.

To use the inhaler the patient presses down on the top of the canister, with their thumb supporting the lower portion of the actuator. Actuation of the device releases a single metered dose of the formulation which contains the medication either dissolved or suspended in the propellant. Breakup of the volatile propellant into droplets, followed by rapid evaporation of these droplets, results in the generation of an aerosol consisting of micrometer-sized medication particles that are then inhaled.

An inhaler (also known as a puffer, pump or allergy spray) is a medical device used for delivering formulations of fenfluramine into the lungs through the work of a person's breathing. This allows formulations of fenfluramine to be delivered to and absorbed in the lungs, which provides the ability for targeted medical treatment to this specific region of the body, as well as a reduction in the side effects of oral medications. There are a wide variety of inhalers, and they are commonly used to treat numerous medical conditions with asthma and chronic obstructive pulmonary disease (COPD) being among the most notable.

Some of the common types of inhalers include metered-dosed inhalers, dry powder inhalers, soft mist inhalers, and nebulizers. Each device has advantages and disadvantages and can be selected based on specific patient needs, as well as age, coordination, and lung function. Proper education on inhaler use is important to ensure that inhaled medication takes its proper effects in the lungs.

Meter-Dosed Inhalers (MDI)

The most common type of inhaler is the pressurized metered-dose inhaler (MDI) which is made up of 3 standard components—a metal canister, plastic actuator, and a metering valve. The medication is typically stored in solution in a pressurized canister that contains a propellant or suspension. The MDI canister is attached to a plastic, hand-operated actuator. On activation, the metered-dose inhaler releases a fixed dose of medication in aerosol form through the actuator and into a patient's lungs. These devices require significant coordination as a person must discharge the medication at or near the same time that they inhale in order for the medication to be effective.

Different Types of Dry Powder Inhalers

Dry Powder Inhalers (DPI)

Dry powder inhalers release a metered or device-measured dose of powdered medication that is inhaled through a DPI device. This device usually contains a chamber in which the powdered medication is deposited prior to each dosage. The powder can then be inhaled with a quick breath. This allows for medication to be delivered to the lungs without the need for use of propellant/suspension.

Soft mist inhalers release a light mist containing medication without the need for a propellant/suspension. Upon pressing a button, the inhaler creates a mist of medication, allowing for inhalation into the lungs. SMIs suspend inhaled medications for roughly 1.2 seconds, which is longer than the average MDI inhaler suspension time period. This requires less coordination when using and may be helpful for young patients or patients that find the MDI inhalers difficult to use.

Nebulizers

Nebulizers are designed to deliver medications over an extended period of time over multiple breaths through a mouthpiece or face mask. They generate a continuous mist with aerosolized medication, allowing a patient to breath normally and receive medications. They are commonly used in infants and toddlers requiring inhaled medications or in patients in the hospital who require inhaled medications.

An echocardiography, echocardiogram, cardiac echo or simply an echo, is an ultrasound of the heart.

Echocardiography uses standard two-dimensional, three-dimensional, and Doppler ultrasound to create images of the heart.

Echocardiography has become routinely used in the diagnosis, management, and follow-up of patients with any suspected or known heart diseases. It is one of the most widely used diagnostic tests in cardiology. It can provide a wealth of helpful information, including the size and shape of the heart (internal chamber size quantification), pumping capacity, and the location and extent of any tissue damage. An echocardiogram can also give physicians other estimates of heart function, such as a calculation of the cardiac output, ejection fraction, and diastolic function (how well the heart relaxes), and further allows a determination of pulmonary artery blood pressure. An echocardiogram can determine if a patient has certain heart value irregularities that would place the patient in a group that fenfluramine should not be administered to. An echocardiogram can also assess pulmonary arterial hypertension which may be related to the respiratory dysfunction brought about the COVID-19 infection. Administration of fenfluramine via any of the pulmonary inhalation technologies described herein can reduce first pass hepatic metabolism of fenfluramine to the metabolite fenfluramine and thus lessen or prevent the side effects of cardiac valvulopathies and/or pulmonary arterial hypertension in a patient receiving fenfluramine inhalation therapy.

Echocardiography is an important tool in assessing wall motion abnormality in patients with suspected cardiac disease. It is a tool which helps in reaching an early diagnosis of myocardial infarction showing regional wall motion abnormality of the heart. Also, it is important in treatment and follow-up in patients with heart failure, by assessing ejection fraction. Patient given formulations of fenfluramine should have a follow-up echocardiogram to confirm that the patient is not developing heart value problems that could be related to the formulations of fenfluramine Echocardiography can help detect pulmonary arterial hypertension (PAH), cardiomyopathies, such as hypertrophic cardiomyopathy, dilated cardiomyopathy, and many others. The use of stress echocardiography may also help determine whether any chest pain or associated symptoms are related to heart disease. The biggest advantage to echocardiography is that it is not invasive (does not involve breaking the skin or entering body cavities) and has no known risks or side effects.

Specific Aspects of the Invention

Provided is a method of treating a patient infected with severe acute respiratory syndrome coronavirus 2 (SARS-CoV-2), comprising: determining the patient has been infected with SARS-CoV-2; and administering to the patient a therapeutically effective dose of fenfluramine.

In one aspect, the administration of fenfluramine via oral, parenteral or inhalation routes prevents or interferes with SARS-CoV-2 replication.

In another aspect, the administration of fenfluramine via oral, parenteral or inhalation routes prevents or lessens scarring in the lungs. In an embodiment, the administration of fenfluramine is via inhalation into the lungs.

In yet another aspect, the administration of fenfluramine is administered prophylactically via oral, parenteral or inhalation routes. In an embodiment, the prophylactic administration is via inhalation into the lungs. In another embodiment, the prophylactic administration is via an oral solid or liquid dosage form.

In still another aspect, the administration of fenfluramine via oral, parenteral or inhalation routes promotes an immune response to SARS-CoV-2 infection.

In some cases, the administering is performed for 5 days or more, such as 10 days or more or 15 days or more.

In some cases, the method further includes administering a co-therapeutic agent. The term "co-therapeutic agent" refers to a compound other than fenfluramine that has a therapeutic effect on a patient who is administered the co-therapeutic agent. In some cases the co-therapeutic agent is selected from the group consisting of: an anti-viral agent, zinc, and an immunomodulatory agent.

The co-therapeutic agent can be an anti-viral agent. In some cases the anti-viral agent is selected from the group consisting of: Remdesivir (a nucleotide analog that acts against SARS-CoV-2 by inhibiting RNA polymerase), a monoclonal antibody, convalescent plasma from a subject who had previously been infected with SARS-CoV-2 and which comprises antibodies for SARS-CoV-2, a viricide, amantadine, rimantadine, and a nucleoside analog. Exemplary nucleoside analogs include acyclovir and zidovudine (AZT). In some cases, the co-therapeutic agent is zinc.

In some cases, the method further includes administering a immunomodulatory co-therapeutic agent. The co-therapeutic agent can be an immunosuppressive agent. Exemplary immunosuppressive agents suppress cytokine production or produce inhibition to regulate the immune response, such as, interleukin-1 (IL-1) inhibitors e.g., anakinra, and/or interleukin-6 (IL-6) inhibitors e.g., toxilizumab, sarilumab or siltuximab.

In some cases, the therapeutically effective dose ranges from 0.5 mg to 500 mg of fenfluramine per day, such as 1 mg to 250 mg, 5 mg to 100 mg, and 10 mg to 50 mg. In some cases, the dose is 250 mg or less per day, such as 100 mg or less, 100 mg or less, or 50 mg or less. In some cases, the dose is 5 mg or more of fenfluramine per day, such as 10 mg or more, or 25 mg or more. In some cases, the dose is part of an aqueous composition. In some cases the therapeutically effective dose is dissolved in water. In some cases the therapeutically effective dose is dispersed in water.

In some cases, the patient is diagnosed with a secondary bacterial infection, and the method further includes administering an antibiotic to the patient.

The dose of fenfluramine administered in the methods of the present invention can be formulated in any pharmaceutically acceptable dosage form including, but not limited to oral dosage forms such as tablets including orally disintegrating tablets, capsules, lozenges, oral solutions or syrups, oral emulsions, oral gels, oral films, buccal liquids, powder e.g. for suspension, and the like; injectable dosage forms; transdermal dosage forms such as transdermal patches, ointments, creams; inhaled dosage forms; and/or nasally, rectally, vaginally administered dosage forms. Such dosage forms can be formulated for once a day administration, or for multiple daily administrations (e.g. 2, 3 or 4 times a day administration).

The dosage form of fenfluramine employed in the methods of the present invention can be prepared by combining fenfluramine with one or more pharmaceutically acceptable diluents, carriers, adjuvants, and the like in a manner known to those skilled in the art of pharmaceutical formulation.

Examples of processes for synthesizing fenfluramine are provided in the following documents: GB1413070, GB1413078 and EP441160. An example of a fenfluramine drug product synthesis is provided in US20180148403 and issued U.S. Pat. Nos. 10,351,509; and 10,351,510 all incorporated herein by reference.

The dose of fenfluramine to be used in a method of the present invention can be provided in the form of a kit, including instructions for using the dose in one or more of the methods of the present invention. In certain embodiments, the kit can additionally comprise a dosage form comprising one or more co-therapeutic agents. The kit may also contain directions for initiating fenfluramine therapy in a patient, in some instances the direction may take into account co-administration with other interacting antiviral drugs and provide alternate dosing instructions when the patient also receives those drugs concomitantly.

In some cases, the fenfluramine is free base fenfluramine. In other cases, the fenfluramine is a pharmaceutically acceptable salt of fenfluramine, such as fenfluramine hydrochloride.

It is known the fenfluramine can have effects on the operation of the heart. Such effects were seen historically mainly in patients treated at daily doses of 60 mg/day or more for a period of months However, it is desirable to assess the risk of administering fenfluramine to the patient and weight these risks versus the potential advantages of administering fenfluramine for treating COVID-19. As such, in some cases the method further comprises performing an echocardiogram (ECHO) and/or an electrocardiogram (EKG) on the patient before the administering, wherein the patient was determined to have a heart healthy enough for administration of fenfluramine.

In some cases the patient is diagnosed with one or more conditions selected from the group consisting of: chronic kidney disease, chronic obstructive pulmonary disease (COPD), pulmonary arterial hypertension, a compromised immune system, a body mass index (BMI) of 30 or more, heart failure, coronary artery disease, cardiomyopathy, sickle cell anemia, and type 2 diabetes mellitus.

In some cases a medical professional has determined that the subject is at risk for experiencing a cytokine storm.

Also provided is a kit comprising a container comprising fenfluramine and instructions directing a healthcare professional to administer the fenfluramine to the patient. In some cases, the fenfluramine is present in an aqueous fluid. In some cases, the kit contains information for the physician of the need to have an echocardiogram performed in order to determine if the patient can safely be treated with fenfluramine. In some cases, the kit contains informs the physician that fenfluramine stimulates an immune response in immunocompromised patients.

Mechanism of Action

Without intending to be limited by any particular mechanism of action, the following describes how fenfluramine aids in the treatment of a patient infected with SARS-CoV-2.

First, fenfluramine impedes the virus's ability to hijack the patient's cellular machinery. The Nsp6 protein of SARS-CoV-2 has been found to interact with sigma-1 and sigma-2 receptors (Gordon et al, Nature, 2020, doi: 10.1038/s41586-020-2286-9), which are proteins at the endoplasmic reticulum (ER). Gordon also reported that drugs which are predicted regulators of sigma-1 and sigma-2 receptors resulted in antiviral activity in several viral assays. Thus, by interfering with the interaction of Nsp6 with sigma-1 reduces the possibility of a SARS-CoV-2 infection.

Furthermore, fenfluramine is a positive modulator of sigma-1 receptors (Martin et al, Epilepsy & Behavior, 2020, doi: 10.1016/j.yebeh.2020.106989). Hence, administration of fenfluramine might inhibit SARS-CoV-2 infectivity by modulating the sigma-1 receptor and preventing it from being successfully used by the Nsp6 protein of SARS-CoV-2.

Second, fenfluramine increases the number and responsiveness of immune cells to SARS-CoV-2. D-fenfluramine has been shown to increase the local immune response to the opportunistic microbial pathogen of *Candida albican* (Mathews et al, Behavior Brain Research, 1996, doi: 10.1016/0166-4328(96)00117-9). Specifically, D-fenfluramine administration resulted in "marked increase in CD3+ and CD8+ lymphocytes [and] a modest increase in the numbers of NK1.1+ cells" (abstract). In addition, long term exposure to D-fenfluramine avoided the age-related decline in levels of natural killer and T cells (Clancy et al, Behavior Brain Research, 1996, doi: 10.1016/0166-4328(96)00114-3). Specifically, 15-month-old rats with long term fenfluramine administration had immune cell levels that were similar to 7-month-old rats that had not received fenfluramine. Hence, fenfluramine increases the number and responsiveness of immune cells.

Third, fenfluramine aids in preventing the body from mounting an overactive immune response, thereby avoiding the dangers of a cytokine storm. Patients with COVID-19 have been observed to have upregulation of pro-inflammatory cytokines including interleukin-1 (IL-1), IL-6, tumor necrosis factor (TNF), TNF-alpha, and interferon-gamma. The highest levels of TNF-alpha, IL-6, and IL-10 have been associated with a more marked reduction in T-cell counts, both CD8+ and CD4+. In addition, it has been observed that fenfluramine administration has suppressed the production of pro-inflammatory cytokines interleukin-1beta and TNF-alpha in response to an in vivo lipopolysaccharide challenge (Connor et al, European Journal of Pharmacology, 2002, doi: 10.1016/S0014-2999(02)02588-8). Hence, fenfluramine administration downregulates some of the pro-inflammatory cytokines, thereby reducing the chance of a dangerous and potentially fatal cytokine storm.

Interleukin-6 (IL-6) is normally secreted transiently in response to injury or infections. However, unregulated synthesis and secretion of IL-6 has contributed to a host of pathological effects such as rheumatoid arthritis. Furthermore, IL-6 induces differentiation of B cells and naïve CD4+ T cells and inhibits TGF-beta differentiation, providing a crucial link between innate and acquired immune responses. These actions place IL-6 in a central role in mediating and amplifying cytokine release syndrome, commonly associated with Ebola and SARS-COV-2 infections, and other types of trauma and infections.

Elevated IL-6 was found to be significantly correlated with death in COVID-19 patients Originally developed for the treatment of arthritis, anti-IL-6R mAbs have been used to treat CRS as a complication of cancer therapy using adaptive T-cell therapies.

The severity of SARS-CoV-1 infection is associated with increased serum concentrations of IL-6 and as such the administration of fenfluramine decreases concentrations of IL-6 and treats adverse effects of SARS-CoV-1 infection.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1: In Vitro Effect of Fenfluramine on Human Lung Epithelial (Calu-3) Cells Infected with SARS-CoV-2

Cell Preparation:

The cell line utilized for the infection was human lung epithelial (Calu-3) cells (ATCC® HTB-55™). These cells were grown from a frozen aliquot of a laboratory working cell line. Passage number is limited to no more than 30 passages from the original aliquot. Cells were grown in T150 flasks in 1×DMEM (ThermoFisher cat. no. 12500062) supplemented with 2 mM L-glutamine (Hyclone cat. no. H30034.01), non-essential amino acids (Hyclone cat. no. SH30238.01), 25 mM HEPES (HyClone cat. no. 16777-032) and 10% Fetal Bovine Serum (FBS) (Atlas Biologicals cat. no. EF-0500-A). Serum was heat-inactivated for infections.

On the day previous to executing the assay, Calu-3 cells were removed from T150 flasks by trypsinization (0.25% Trypsin, Corning cat. no. 25-053-C1) and measured for count and viability by Hemocytometer in trypan blue. Cells were resuspended to 1.3×105 cells/mL in 1×DMEM, and plated at 150 µl (0.15 mLs) per well for a density of 20,000 cells/well in 96 well plate. The plates were then incubated for approximately 24 hours to allow cell adherence at 37° C., 5% CO2. Cell passage used was 20.

Virus Stocks:

The virus strain used for the assay was the mNeonGreen SARS-CoV-2 provided by the World Reference Center for Emerging Viruses and Arboviruses at the University of Texas Medical Branch, Galveston, Tex. (Xie et al, 2020). This reporter virus was constructed from the virus strain (2019-nCoV/USA_WA1/2020) isolated from the first reported SARS-CoV-2 case in the US (Harcourt et al., 2020, Holshue et al., 2020). Virus stocks were amplified in Vero E6 cells to Passage 1 (P1) with a titer of 9.7×105 PFU/mL. Stocks were stored at −80° C. Virus infection of indicated wells were carried out with an MOI=0.5 and 0.1.

Assay Setup:

1. Fenfluramine was diluted to 50 µM in cell culture media which is described above.

2. Pre-treatment: Media was aspirated from the 96 wells, 100 µL of the compound dilution (and vehicle control) was added to cells as shown above in the plate map, and the plate(s) incubated at 37° C./5% $CO_2$ for 1 hour.

3. After the pre-treatment, virus (MOI 0.5 or 0.1, see plate map) was added dropwise into the media, plates were sealed with Aeroseal and incubated for 72 hr at 37° C./5% CO2.

4. Cytotoxicity assays were conducted in parallel, for these no virus was added.

5. At 72 hr, supernatants were harvested and stored at −80 C. Infected cells were imaged using the Celigo imaging Cytometer (Nexcelom Bioscience).

a. Cell viability: was assessed by staining cells with the ViaStain™ Calcein AM/Hoechst/PI Viability Kit (Nexcelom, Cat #CS5-V006-1) per manufacturer's instructions and imaging with the Celígo Imaging Cytometer (Nexcelom). Briefly, live and metabolically active cells were detected using the Calcein AM stain (Ex/Em: 488/520). Dead cells were detected using the propidium iodide stain (PI, Ex/Em: 493/636). Total number of cells were detected using the Hoechst-nuclear stain (Ex/Em: 352/461). Thus, cell viability was assessed by comparing live cells counts (normalized to total cell count) across treatment groups, and cell cytotoxicity was assessed through comparison of dead cell counts (normalized to total cells) across treatment groups.

b. Viral replication: cells were infected with the mNeonGreen SARS-CoV-2 reporter virus (provided by The World Reference Center for Emerging Viruses and Arboviruses at the University of Texas Medical Branch, Galveston, Tex.). Following infection for 72 hr, media was aspirated from cells, and cells were washed with 1×PBS. Cells were then stained with Hoechst nuclear stain (Nexcelom, Cat #CS1-0128) according to manufacturer's instructions and imaged with the Celígo Imaging Cytometer (Nexcelom). SARS-CoV-2 replication was detected and quantified using the mNeonGreen reporter fluorescence (Ex/Em: 506/517 nm). The total number of cells were quantified using Hoechst-nuclear staining (Ex/Em: 352/461). Reporter expression values (fluorescence at 517 nm) were normalized to total cell count, and then compared among treatment groups.

Figure 1B:
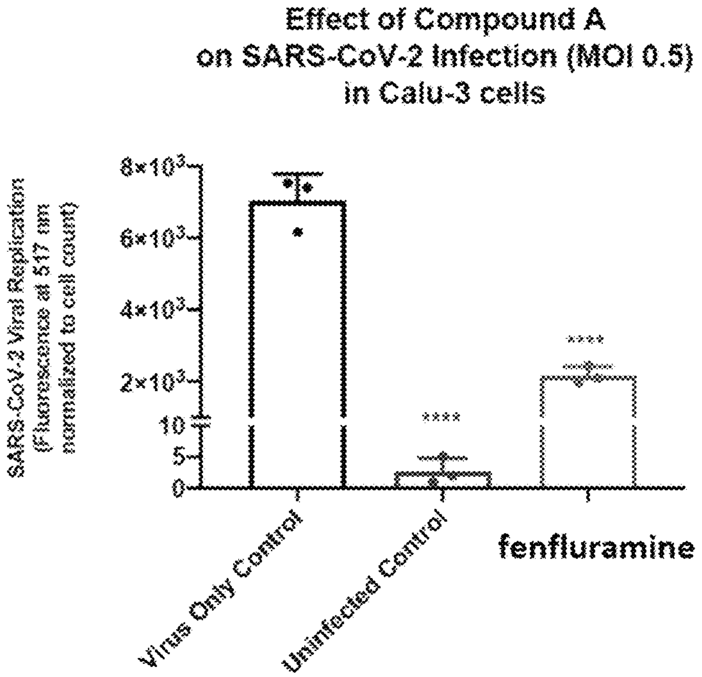
FIG. 1B shows data relating to FIG. 1A of quantification of fluorescence in infected versus control wells (average of three wells per treatment). One-way ANOVA with Dunnett's multiple comparisons test was conducted with Compound A treatment compared to the Virus only control (****=p<0.0001).
Figure 2A:
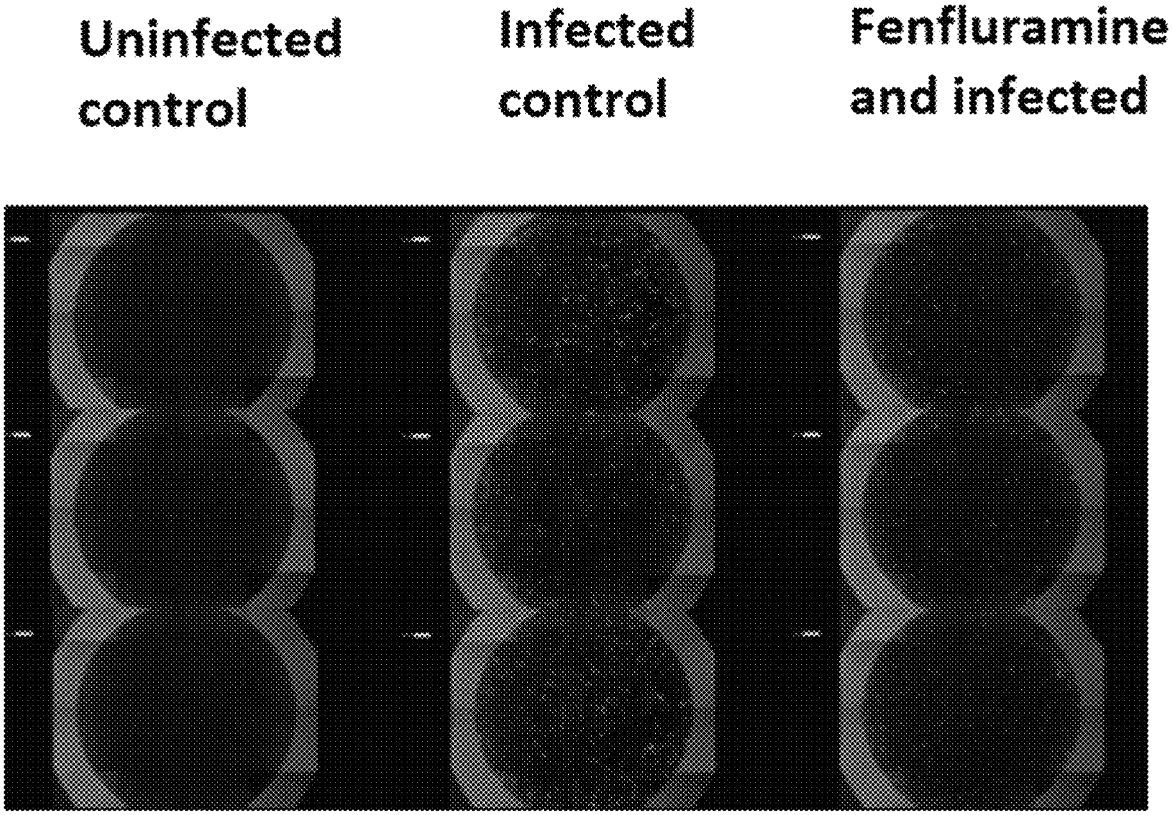
FIG. 2A shows viral replication measured by quantification of mNeonGreen fluorescence of the SARS-CoV-2 reporter virus in infected Calu-3 cells in the presence and absence of Compound A treatment (50 mM). Multiplicity of infection=0.1. 2A. images of infected and controls wells.
Figure 2B:
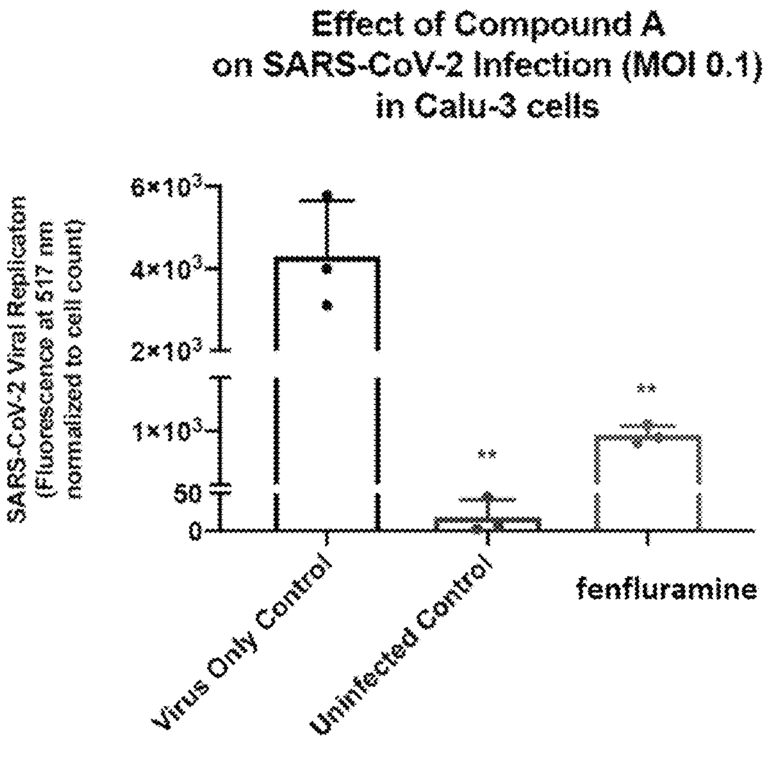
FIG. 2B shows data relating to FIG. 2A of quantification of fluorescence in infected versus control wells (average of three wells per treatment). One-way ANOVA with Dunnett's multiple comparisons test was conducted with Compound A treatment compared to the Virus only control (****=p<0.0001).

Results:

It was found SARS-CoV-2 viral replication was statistically significantly ($p<0.0001$) lower in samples of Calu-3 cells that were administered 50 mM of fenfluramine compared control cells receiving only vehicle. In particular, the average viral replication for the control cells was approximately $7\text{-}10^3$ whereas the average viral replication for the fenfluramine-contacted cells was about $2\cdot10^3$, as shown in FIG. 1B. In addition, FIG. 1A shows exemplary images of uninfected, control infected, and infected but also administered 50 μM fenfluramine cells. FIGS. 1A and 1B correspond to a multiplicity of infection (MOI) of 0.5 whereas FIGS. 2A and 2B correspond to a MOI of 0.1.

Figure 3A:
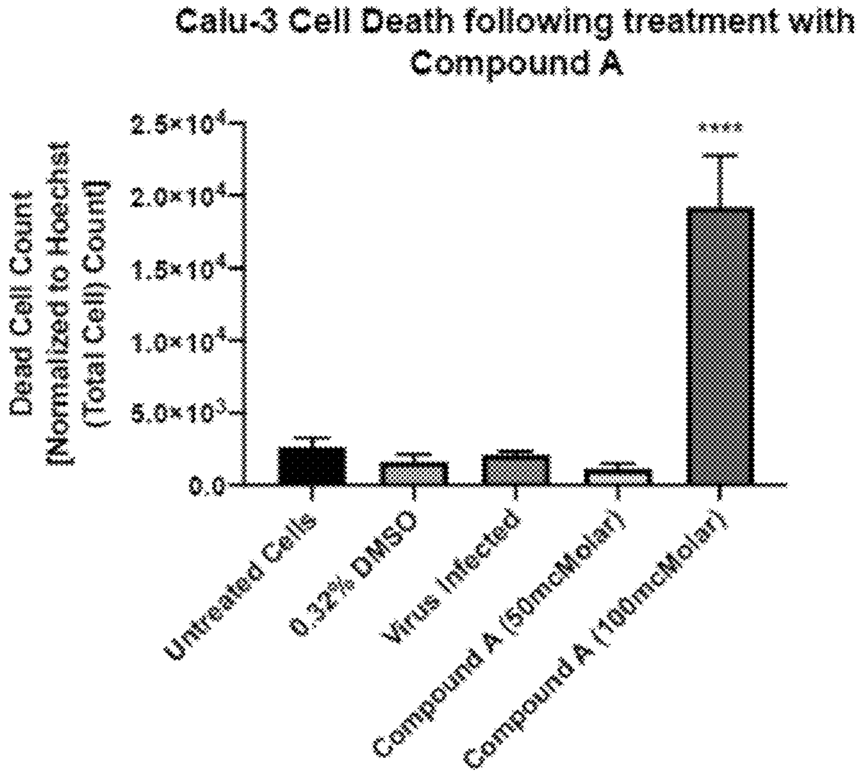
FIG. 3A shows cell death and viability following treatment of Calu-3 cells with Compound A treatment (50 μM). 3A. Cell death measured using propidium iodide staining normalized to total cell count measured by Hoeschst staining.
Figure 3B:
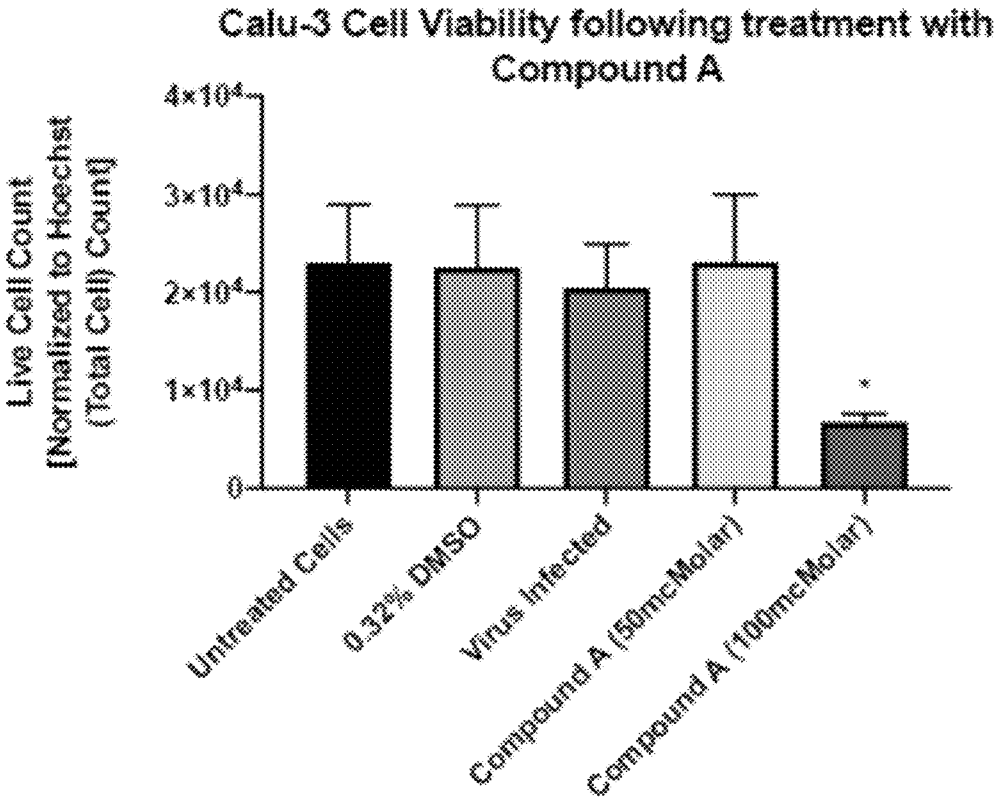
FIG. 3B shows data relating to FIG. 3A of cell viability measured using acridine orange staining normalized to total cell count measured by Hoeschst staining. One-way ANOVA with Dunnett's multiple comparisons test was conducted with Compound A treatment compared to the Virus only control (*=p=0.0140, ****=p<0.0001). Compound A at 20 μg/ml is not cytotoxic and shows cell death and viability similar to controls. Compound A at 40 μg/ml is cytotoxic and shows statistically significant higher levels of cell death and low cell viability compared to controls. Compound A is fenfluramine.

FIGS. 3A and 3B show additional experiments measuring cell death under different conditions. Compound A in the figures is fenfluramine.

It is hypothesized that fenfluramine has the lysosomotropism property. Fenfluramine might act as a positive allosteric modulator of sigma-1. Vela, Jose Miguel (Frontiers in Pharmacology, 2020, 11:582310, "Repurposing Sigma-1 Receptor Ligands for COVID-19 Therapy?", doi: 10.3389/fphar.2020.582310), describes sigma-1 ligands and lysosomotropism.

Example 2: In Vitro Effect of Fenfluramine on Vero E6 Cells Infected with SARS-CoV-2

Cell Preparation:

The cell line utilized for the infection and plaque assays is Vero E6 cells (ATCC® CRL-1586). These cells were grown from a frozen aliquot of a laboratory working cell line. Passage number is limited to no more than 50 passages from the original aliquot. Cells were grown in T150 flasks in 1×DMEM (ThermoFisher cat. no. 12500062) supplemented with 2 mM L-glutamine (Hyclone cat. no. H30034.01), non-essential amino acids (Hyclone cat. no. SH30238.01), and 10% heat inactivated Fetal Bovine Serum (FBS) (Atlas Biologicals cat. no. EF-0500-A).

On the day previous to executing the assay, Vero E6 cells were removed from T150 flasks by trypsinization (0.25% Trypsin, Corning cat. no. 25-053-C1) and measured for count and viability by Hemocytometer in trypan blue. Cells were resuspended to 2.3×105 cells per mL in 1×DMEM (supplemented as indicated above) and plated at 0.15 mLs per well (35,000 cells/well) in 96-well plates. The plates were then incubated for approximately 24 hours to allow cell adherence at 37° C., 5% CO2.

Virus Stocks:

The virus strain used for the assay was SARS-CoV2, USA WA 01/2020, CSU V2 03/17/202 passage 3. Virus stocks were obtained from BEI Resources and amplified in Vero E6 cells to Passage 3 (P3) with a titer of 5.5×105 PFU/mL. Stocks were stored at −80° C. Virus infection of indicated wells were carried out with an MOI=0.1.

3. Pre-treatment: Media was aspirated from the 96 wells, 100 □L of the compound dilutions (and controls) as shown above in the plate map were added, and the plate(s) incubated at 37° C./5% CO2 for 1 hr.

4. After the pre-treatment, virus (MOI 0.1) was added dropwise into the media, plates were sealed with Aeroseal and incubated for 72 hr at 37° C./5% CO2. For cytotoxicity assays, no virus was added.

5. At 72 hr, supernatants were harvested and stored at −80 C. Cytoprotection was measured using neutral red.

a. Neutral red (NR) solution (0.33% NRS, Sigma Aldrich cat. no. N2889) maintained at room temperature was diluted 1:24 in 10% 1×DMEM warmed to 37° C. Immediately after dilution the solution was centrifuged at 4000 rpm in a table top centrifuge for 30 min (to remove any NR crystals)

b. The diluted NR solution was added to the cells (150 □l/well)

c. The plate was incubated at 37° C., 5% CO2 for approximately 2 hours d. NR solution was removed, and NR solubilization solution (1% glacial acetic acid in 50% ethanol) was added to each well at 150 μl/well. Plates were incubated at room temperature for 10 minutes, and solubilization solution mixed by pipetting e. 130 μL from each well was transferred to a new plate f. Absorbance was read on a plate reader at 540 nm.

Figure 4A:
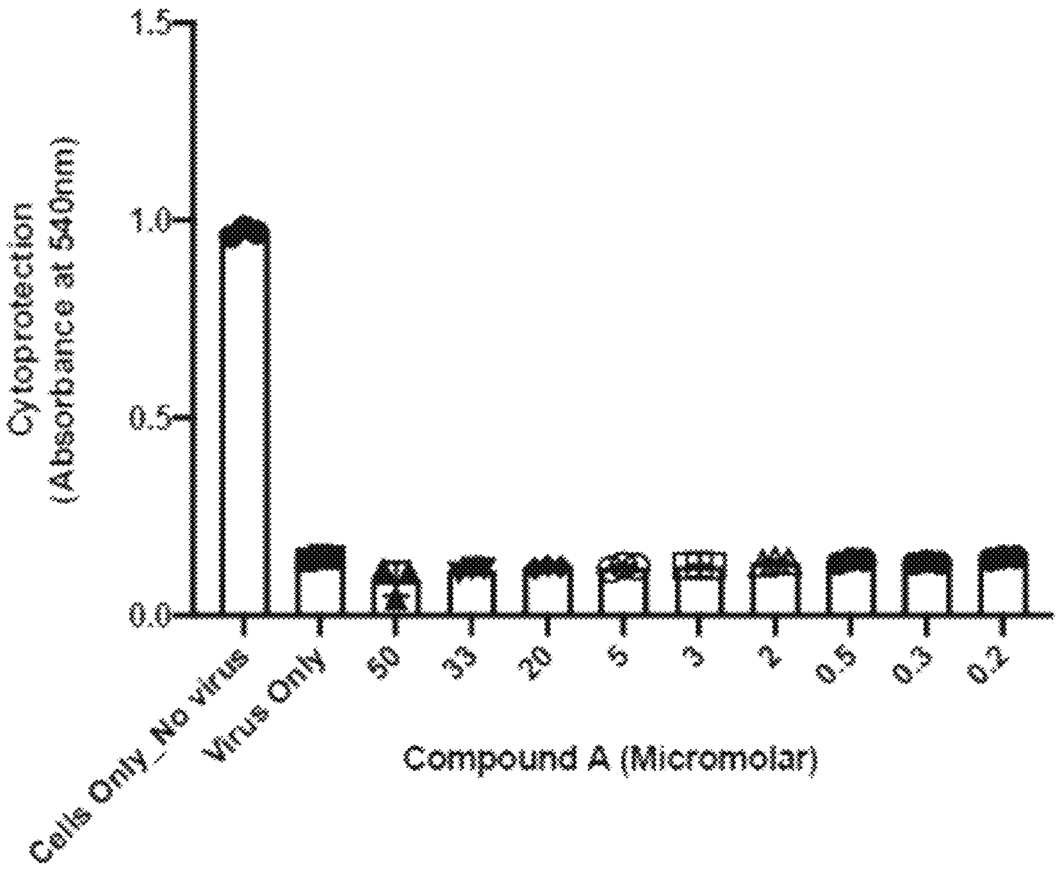
FIG. 4A shows cytoprotection and cytotoxicity in Vero E6 cells infected with SARS-CoV-2 following treatment with fenfluramine and as measured using neutral red. In particular, shown is dose response to infected cells. Compound A is fenfluramine.
Figure 4B:
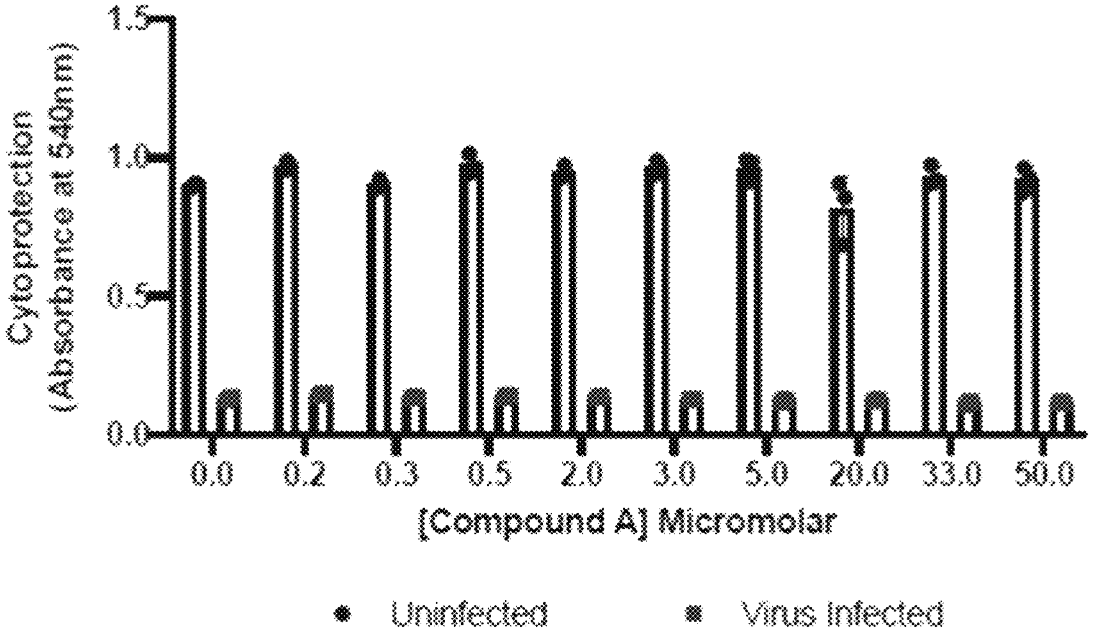
FIG. 4B shows cytoprotection and cytotoxicity in Vero E6 cells infected with SARS-CoV-2 following treatment with fenfluramine and as measured using neutral red. In particular, shown dose response to infected cells compared to uninfected cells. Compound A is fenfluramine. The upper dots near 1.0 are uninfected cells and the lower dots near 0.2 are virus infected.

Results:

FIGS. 4A and 4B show cytoprotection and cytotoxicity in Vero E6 cells infected with SARS-CoV-2 following treatment with fenfluramine as measured using neutral red.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art and are to be construed as being without limitation to such specifically recited examples and conditions.

Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of treating a patient infected with severe acute respiratory syndrome coronavirus 2 (SARS-CoV-2), comprising:

determining the patient has been infected with SARS-CoV-2; and administering to the patient a therapeutically effective dose of fenfluramine.

2. The method of claim 1, wherein the administering is performed for 5 days or more.

3. The method of claim 2, wherein the administering is performed for 10 days or more.

4. The method of claim 1, further comprising:

administering a co-therapeutic agent.

5. The method of claim 4, wherein the co-therapeutic agent is an anti-viral agent.

6. The method of claim 5, wherein the anti-viral agent is remdesivir.

7. The method of claim 5, wherein the anti-viral agent is a monoclonal antibody.

8. The method of claim 5, wherein the anti-viral agent is convalescent plasma from a subject who had previously been infected with SARS-CoV-2 and which comprises antibodies for SARS-CoV-2.

9. The method of claim 5, wherein the anti-viral agent is a viricide.

10. The method of claim 5, wherein the anti-viral agent is amantadine.

11. The method of claim 5, wherein the anti-viral agent is rimantadine.

12. The method of claim 5, wherein the anti-viral agent is a nucleoside analog.

13. The method of claim 12, wherein the nucleoside analog is acyclovir or zidovudine (AZT).

14. The method of claim 4, wherein the co-therapeutic agent is zinc.

15. The method of claim 1, wherein the therapeutically effective dose ranges from 0.5 mg to 500 mg of fenfluramine per day.

16. The method of claim 15, wherein the therapeutically effective dose ranges from 5 mg to 100 mg of fenfluramine per day.

17. The method of claim 1, wherein the patient is diagnosed with a secondary bacterial infection, further comprising administering an antibiotic to the patient.

18. The method of claim 1, wherein the patient is diagnosed with one or more conditions selected from the group consisting of: chronic kidney disease, chronic obstructive pulmonary disease (COPD), a compromised immune system, a body mass index (BMI) of 30 or more, heart failure, coronary artery disease, cardiomyopathy, sickle cell anemia, and type 2 diabetes mellitus.

19. The method of claim 1, further comprising performing an echocardiogram (ECHO) on the patient before the administering, wherein the patient was determined to have a heart healthy enough for administration of fenfluramine and no signs of pulmonary arterial hypertension.

20. The method of claim 1, wherein the administering involves directing an aerosolized aqueous fenfluramine composition directly to a lung of the patient.

* * * * *